(12) United States Patent
Wissner-Gross et al.

(10) Patent No.: US 11,737,701 B2
(45) Date of Patent: Aug. 29, 2023

(54) METHODS, SYSTEMS AND MEDIA FOR RECONSTRUCTING BIOELECTRONIC LEAD PLACEMENT

(71) Applicant: BioSig Technologies, Inc., Westport, CT (US)

(72) Inventors: Alexander David Wissner-Gross, Cambridge, MA (US); Suraj Kapa, Rochester, MN (US); James Y. Lee, Stamford, CT (US); Desmond B. Keenan, Stevenson Ranch, CA (US); Natalia Drapeau, Geneva (CH); Kenneth L. Londoner, Westport, CT (US)

(73) Assignee: BioSig Technologies, Inc., Westport, CT (US)

( * ) Notice: Subject to any disclaimer, the term of this patent is extended or adjusted under 35 U.S.C. 154(b) by 15 days.

(21) Appl. No.: 17/240,809

(22) Filed: Apr. 26, 2021

(65) Prior Publication Data

US 2021/0345933 A1 Nov. 11, 2021

Related U.S. Application Data

(60) Provisional application No. 63/018,307, filed on Apr. 30, 2020.

(51) Int. Cl.
*A61B 5/00* (2006.01)
*A61B 5/349* (2021.01)
*A61B 5/389* (2021.01)
*A61B 5/327* (2021.01)

(52) U.S. Cl.
CPC ............. *A61B 5/349* (2021.01); *A61B 5/327* (2021.01); *A61B 5/389* (2021.01)

(58) Field of Classification Search
CPC .......... A61B 5/349; A61B 5/327; A61B 5/389
See application file for complete search history.

(56) References Cited

U.S. PATENT DOCUMENTS

| | | | | |
|---|---|---|---|---|
| 7,123,954 | B2* | 10/2006 | Narayan | A61N 1/3625 600/518 |
| 9,002,442 | B2* | 4/2015 | Harley | A61B 5/318 600/509 |
| 2004/0059237 | A1* | 3/2004 | Narayan | A61B 5/35 607/9 |
| 2007/0021679 | A1* | 1/2007 | Narayan | A61B 5/35 600/518 |
| 2020/0000355 | A1* | 1/2020 | Khair | A61B 5/296 |

* cited by examiner

*Primary Examiner* — Shirley X Jian
(74) *Attorney, Agent, or Firm* — Sterne, Kessler, Goldstein & Fox P.L.L.C.

(57) ABSTRACT

Methods, systems, and media are disclosed for reconstructing bioelectronic lead placement. In some embodiments, the disclosed system can include a processor configured to determine relationships between EP signals of one or more pairs of a plurality of electrodes over one or more sampling time periods, wherein the plurality electrodes are separately placed on a patient's body for collecting the EP signals, and to reconstruct geometry of the plurality of electrodes based on the relationships between the EP signals.

30 Claims, 25 Drawing Sheets

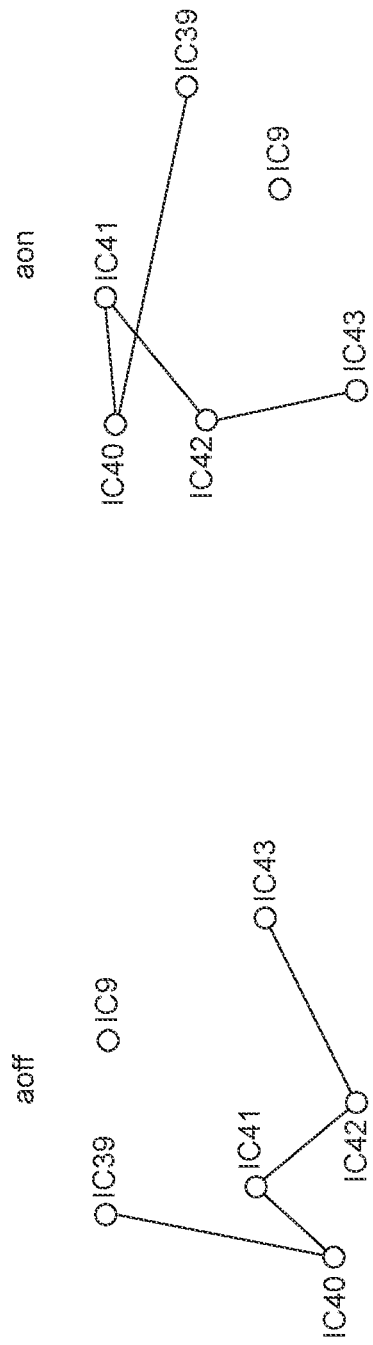
FIG. 6I
FIG. 6J
FIG. 6K
FIG. 6L

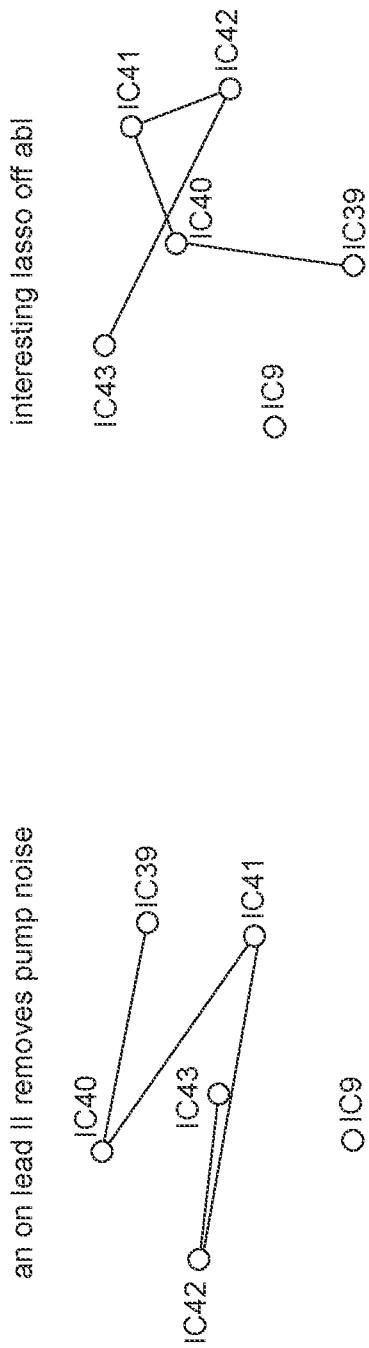

METHODS, SYSTEMS AND MEDIA FOR RECONSTRUCTING BIOELECTRONIC LEAD PLACEMENT

CROSS-REFERENCE TO RELATED APPLICATIONS

This U.S. Non-Provisional patent application claims the benefit of U.S. Provisional Patent Application No. 63/018,307, which was filed on Apr. 30, 2020, the entire content of which is incorporated herein by reference.

FIELD

Embodiments included herein generally relate to methods, systems and media for reconstructing bioelectronic lead placement. More particularly, embodiments relate to hardware and software for reconstructing spatial distribution of multiple electrophysiology (EP) leads based on relationship analyses between EP signals.

BACKGROUND

Electrophysiology is an electrical recording technique that enables the measurement and study of electrical properties of biological cells and tissues. Specifically, cardiac electrophysiology (EP) signals, including surface electrocardiogram (SECG) and intracardiac electrocardiogram (IECG) signals, are used by cardiologists to analyze cardiac electrical activity, allowing the cardiologists to measure irregular rhythms during cardiovascular activity and diagnose heart diseases. EP monitoring devices have been developed to facilitate rapid response to life-threatening arrhythmias in patients with acute myocardial infarction. EP monitoring has become widely available in various hospital units, such as intensive care environments, ambulatory telemetry units, operating theatres, and emergency rooms. Multi-lead EP monitoring, such as electrocardiography, has been developed for detection of complex arrhythmias, identification of prolonged QT intervals, and ST-segment/ischemia monitoring, etc.

However, the leads/electrodes of a multi-lead EP device need to be attached at specific positions for the resulting signals to be useful. Not only can misplaced electrodes result in incorrect readings, but the placement of multiple surface leads/electrodes on the patient's limbs and chest, or the placement of multiple intracardiac leads/electrodes directly on cardiac tissue of the patient, may be disturbed due to the patient's movement during long-term monitoring or in a surgery.

SUMMARY

Methods, systems and media for reconstructing the spatial location/distribution of multiple EP leads/electrodes based on collected EP signals from the EP leads/electrodes are provided. Methods, systems and media for automatically recommending optimal EP leads/electrodes placement based on the reconstruction are also provided.

One aspect of the present disclosure provides a system for reconstructing bioelectronic lead placement. The system comprises a processor configured to determine relationships between EP signals of one or more pairs of a plurality of electrodes over one or more sampling time periods, the plurality of electrodes having been positioned on a patient's body for collection of the EP signals, and to reconstruct geometry of the plurality of electrodes based on the relationships between the EP signals.

In some embodiments, the plurality of electrodes include surface electrodes configured to collect surface electrocardiogram (SECG) signals.

In some embodiments, the plurality of electrodes include intracardiac electrodes configured to collect intracardiac electrocardiogram (IECG) signals.

In some embodiments, the processor is further configured to determine biological signaling time latencies between the EP signals of the one or more pairs of the plurality of electrodes.

In some embodiments, the processor is further configured to determine Pearson correlation coefficients between the EP signals of the one or more pairs of the plurality of electrodes.

In some embodiments, the processor is further configured to fit the relationships to a weighted graph in which the plurality of electrode are nodes and the relationships are edges.

In some embodiments, the processor is further configured to apply a Fruchterman-Reingold optimization method to fit the weighted graph in a two or three dimensional embedded space.

In some embodiments, the processor is further configured to determine a classification of a patient condition based on the reconstructed geometry of the plurality of electrodes.

In some embodiments, the processor is further configured to determine a misplacement of one or more electrodes of the plurality of electrodes based on the reconstructed geometry of the plurality of electrodes.

In some embodiments, the processor is further configured to correct a misplacement of at least one of two electrodes of the plurality of electrodes to fix a vector orientation between the two electrodes.

In some embodiments, the processor is further configured to recommend a change in placement of one or more electrodes in the plurality of electrodes.

Another aspect of the present disclosure provides a method for reconstructing bioelectronic lead placement. The method comprises acquiring EP signals collected from a plurality of electrodes, determining relationships between the EP signals of one or more pairs of the plurality of electrodes over one or more sampling time periods, and reconstructing a geometry of the plurality of electrodes based on the relationships between the EP signals.

In some embodiments, the acquiring of the EP signals comprises acquiring electrocardiogram (ECG) signals and the plurality of electrodes include surface electrodes.

In some embodiments, the acquiring of the EP signals comprises acquiring intracardiac electrocardiogram (IECG) signals, and the plurality electrodes include intracardiac electrodes.

In some embodiments, the relationships are biological signaling time latencies between EP signals of the one or more pairs of the plurality of electrodes.

In some embodiments, the relationships are Pearson correlation coefficients between EP signals of the one or more pairs of the plurality of electrodes.

In some embodiments, reconstructing the geometry of the plurality of electrodes includes fitting the relationships to a weighted graph in which the plurality of electrodes are nodes and the relationships are edges.

In some embodiments, reconstructing the geometry of the plurality of electrodes includes applying a Fruchterman-Reingold optimization method to fit the weighted graph in a two or three dimensional embedded space.

In some embodiments, the method further comprises determining a classification of a patient condition based on the reconstructed geometry of the plurality of electrodes.

In some embodiments, the method further comprises determining a misplacement of one or more electrodes in the plurality of electrodes based on the reconstructed geometry of the plurality of electrodes.

In some embodiments, the method further comprises correcting a misplacement of at least one of two electrodes in the plurality of electrodes to fix a vector orientation between the two electrodes.

In some embodiments, the method further comprises recommending a change in placement of one or more electrodes in the plurality of electrodes.

Another aspect of the present disclosure provides a non-transitory computer-readable medium containing computer-executable instructions that, when executed by a hardware processor, cause the hardware processor to perform a method for reconstructing bioelectronic lead placement. The method comprises acquiring EP signals collected from a plurality of electrodes, determining relationships between the EP signals of one or more pairs of the plurality of electrodes over one or more sampling time periods, and reconstructing a geometry of the plurality of electrodes based on the relationships between the EP signals.

Other aspects of the present disclosure can be understood by those skilled in the art in light of the description, the claims, and the drawings of the present disclosure.

BRIEF DESCRIPTION OF THE DRAWINGS

The accompanying drawings, which are incorporated herein and form part of the specification, illustrate the present embodiments and, together with the description, further serve to explain the principles of the present embodiments and to enable a person skilled in the relevant art(s) to make and use the present embodiments.

Figure 1:
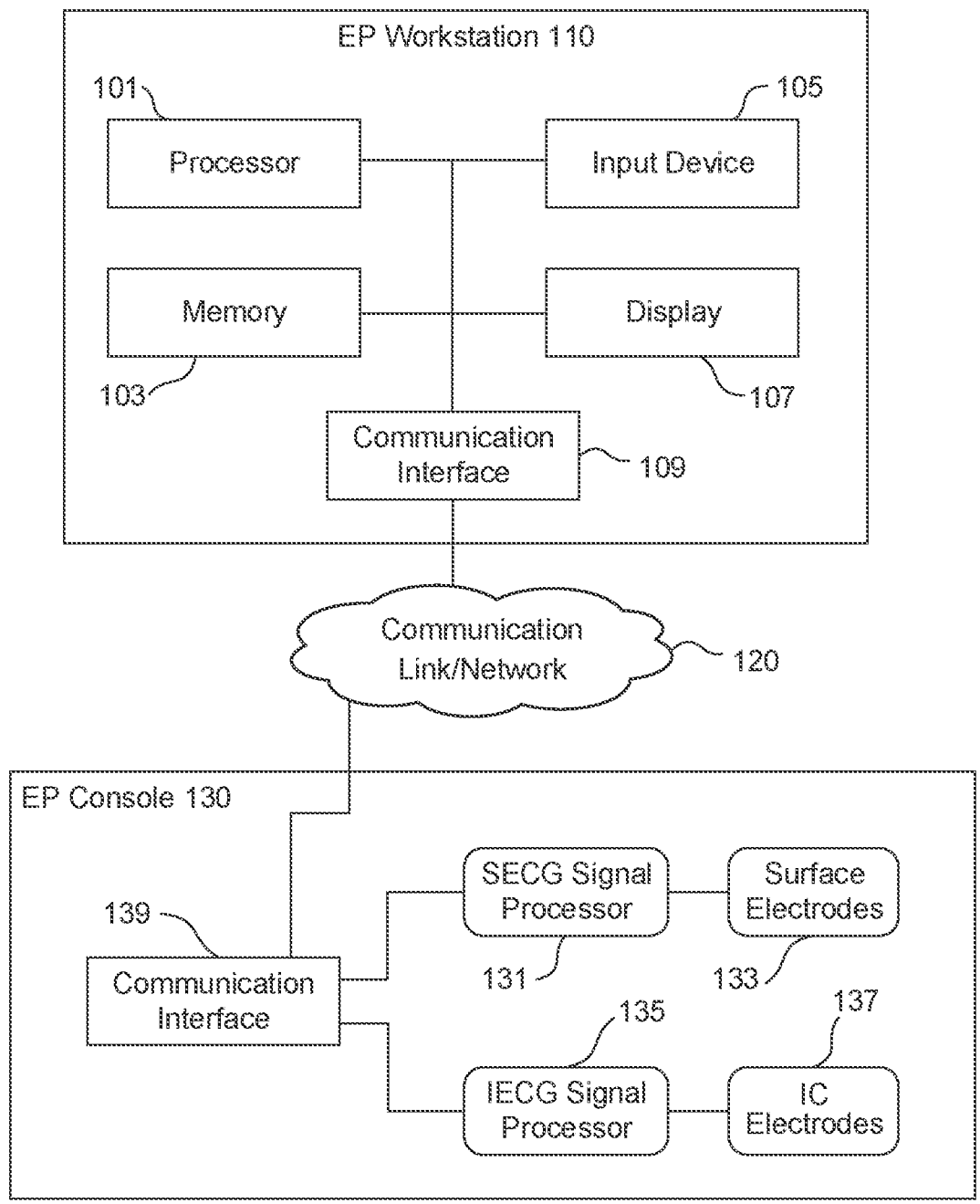
FIG. 1 illustrates a block diagram of a hardware system including an EP workstation and an EP console, in accordance with some embodiments of the disclosed subject matter.

The features and advantages of the present embodiments will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present disclosure. It will be apparent to a person skilled in the pertinent art that the present disclosure can also be employed in a variety of other applications.

It is noted that references in the specification to "one embodiment," "an embodiment," "an example embodiment," "some embodiments," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of a person skilled in the pertinent art to effect such feature, structure or characteristic in connection with other embodiments whether or not explicitly described.

In general, terminology may be understood at least in part from usage in context. For example, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context.

Methods, systems, and media are disclosed for reconstructing bioelectronic lead placement.

This disclosure refers to electrophysiology (EP) signals (e.g., cardiac EP signals, electroneuronographic signals, etc.) taken from potential differences recorded at two (or more) different, separated electrodes that are placed on or in a patient's body. For example, the EP signals can include SECG signals measured from surface leads placed on limbs and chest of the patient. As another example, the EP signals can include IECG signals measured from intracardiac (IC) leads, which may include one or more separate catheters placed directly on cardiac tissue of the patient. As yet another example, the EP signals can include electroneuronographic (ENOG) signals such as deep brain stimulation (DBS) signals from DBS leads on a lead wire implanted into a specific brain area of the patient, spinal cord stimulation (SCS) signals from SCS leads placed under the skin of the patient, and/or sacral neuromodulation (SNM) signals from SNM leads on a lead wire implanted near the sacral nerve of the patient, etc.

The disclosed methods, systems, and media can automatically recommend and evaluate lead/electrode placement on/in the patient, and provide a simplified visual summary of EP signal recordings and automated classification of patient conditions based on a spatial map of the multiple leads/electrodes.

In various embodiments, raw bioelectronic signals from the two (or more) different, separated leads/electrodes placed on or in a patient's body can be collected. The correlations between signal data from different leads/electrodes can be analyzed to reconstruct spatial information about the leads/electrodes. Specifically, time lag relationships between the multiple leads/electrodes over periods of time can be calculated, and the time lag relationships can be fitted to a weighted graph structure in which the leads/electrodes are nodes and the time lag relationships are edges. As such, a spatial map of the leads/electrodes can be accurately reconstructed either in a two-dimensional (2D) embedded space or in a three-dimensional (3D) embedded space. Patient conditions can be determined based on the reconstructed spatial map of the leads/electrodes. This disclosure identifies both hardware and software embodiments to achieve these objectives.

FIG. 1 is a block diagram representing an example hardware system 100, including, for example, an EP workstation 110 and an EP console 130 that can be connected via a communication link/network 120, in accordance with some embodiments of the disclosed subject matter.

As shown in FIG. 1, EP workstation 110 can include user input, visualization, and review functionalities. For example, EP workstation 110 can include one or more processors 101, memory 103, one or more local and/or remote displays 107, one or more input devices 105, and a communication interface 109, which can be interconnected via a communication infrastructure or bus (not shown).

One or more processors 101 can use a computer program to execute the mechanisms described herein, including performing the method for reconstructing bioelectronic lead placement as described below in connection with FIG. 2; sending and/or receiving data through communications interface 109; sending and/or receiving raw EP signals transmitted by an EP console 130; and/or performing any other suitable actions. In some embodiments, one or more processors 101 can send and receive data through communications interface 109 or any other communication links using, for example, a transmitter, a receiver, a transmitter/receiver, a transceiver, or any other suitable communication device.

In some embodiments, memory 103 can include a storage device (such as a computer-readable medium) for storing a computer program for controlling processor 101. In some embodiments, one or more local and/or remote displays 107 can include a touchscreen, a flat panel display, a projector, a speaker, and/or any other suitable display and/or presentation devices for providing display capability for EP signal visualization and review software. One or more input devices 105 can include, for example, a computer keyboard, a mouse, a key pad, a remote control, a microphone, a touchscreen, and/or any other suitable input device as would be used by a designer of input systems or process control systems.

EP console 130 can include multiple electrodes configured to be placed on various locations on or in a patient's body for collecting or measuring electrophysiology (EP) signals (e.g., cardiac EP signals, electroneuronographic signals, etc.) of the patient. EP console 130 can include one or more signal processors to process the EP signals from the multiple electrodes.

In some embodiments as shown in FIG. 1, EP console 130 can include one or more surface electrocardiogram (SECG) signal processors 131 to process SECG signals recorded from a plurality of surface electrodes 133 on a patient's skin. Additionally or alternatively, EP console 130 can include one or more IECG signal processors 135 to process IECG signals recorded from a plurality of intracardiac (IC) electrodes 137 inside the patient's heart. Both raw SECG signals and IECG signals may be small analog signals that require conditioning and amplification to be accurately evaluated and transformed to digital signals.

It is noted that the structure of EP console 130 used for collecting cardiac EP signals, as shown in FIG. 1, is merely used as an example for demonstrative purpose, but does not limit the scope of the present disclosure. As discussed above, the EP signal can additionally or alternatively include various electroneuronographic (ENOG) signals. Therefore, in some alternative embodiments, EP console 130 can include any suitable ENOG signal detecting system (not shown in FIG. 1), such as deep brain stimulation (DBS) signal detecting system, spinal cord stimulation (SCS) signal detecting system, sacral neuromodulation (SNM) signal detecting system, etc. In some alternative embodiments, EP console 130 can be an integrated system including any suitable combination of various subsystems for detecting various EP signals, respectively.

Communications network 120 can be any suitable wired or wireless (or a combination thereof) computer network or combination of networks including the Internet, an intranet, a wide-area network ("WAN"), a local-area network ("LAN"), a wireless network, a digital subscriber line ("DSL") network, a frame relay network, an asynchronous transfer mode ("ATM") network, a virtual private network ("VPN"), etc.

Communication interfaces 109 and 139 can be any interfaces suitable for communicating data between EP workstation 110 and EP console 130. Communication interfaces 109 and 139 can enable EP workstation 110 and EP console 130 to communicate and interact with any combination of external devices, external networks, external entities, etc. EP workstation 110 and EP console 130 can be located in a same location or remotely separated.

Figure 2:
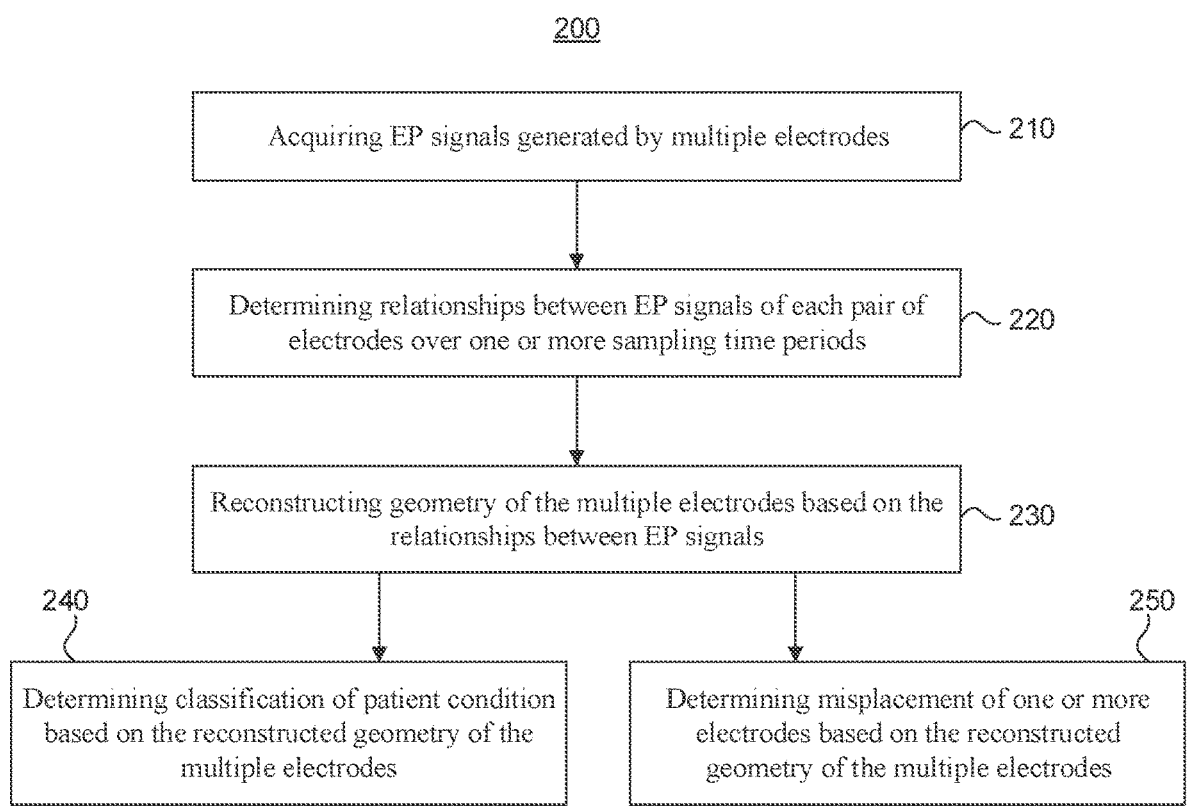
FIG. 2 illustrates a flowchart of an example method for reconstructing bioelectronic lead placement, in accordance with some embodiments of the disclosed subject matter.

Referring to FIG. 2, a flowchart of an example method 200 for reconstructing bioelectronic lead placement is shown in accordance with some embodiments of the disclosed subject matter.

Method 200 can start at operation 210, in which EP signals can be acquired. It is noted that cardiac EP signals, such as electrocardiography (ECG) signals, are used as an example and a representative for the EP signals in the following description of method 200 for demonstrative propose, but this should not limit the disclosed subject matter. Method 200 can be applied to any other suitable EP signals, including, but not limited to electroneuronographic (ENOG) signals, electroencephalographic (EEG) signals, electromyographic (EMG) signals, electrooculography (EOG) signals, electrocochleographic (ECOG) signals, electrogastrographic (EGG) signals, electrogastroenterographic (EGEG) signals, electrohysterographic (EHG) signals, electropneumographic (EPG) signals, electrospinographic (ESG) signals, etc.

In some embodiments, as discussed above in connection with FIG. 1, the EP signals, including SECG signals and/or IECG signals, can be directly collected by an EP console. For example, row analog ECG signals can be detected by a plurality of surface electrodes and/or IC electrodes. The row analog ECG signals can then be processed by one or more SECG signal processors and/or IECG signal processors. For example, the row analog ECG signals can be amplified by one or more ECG signal amplifiers, and then converted to digital ECG signals by an analog-to-digital converter.

In some alternative embodiments, the EP signals can be acquired from a database through a network. One example database from which cardiac EP signals can be acquired is the PhysioNet 2020 Challenge Training Dataset for artificial intelligence (AI) algorithm training purposes.

It is noted that, when applied to ECG signals, the disclosed method 200 can be applied to either SECG signals or IECG signals, or a combination thereof. In the following description, the SECG signals are mainly discussed for simplicity, since the surface leads for collecting SECG signals are placed directly on the surface of a patient's body. In particular, since a 12-lead surface ECG is utilized as a gold standard tool to diagnose cardiovascular diseases such as myocardial infarction and atrial fibrillation, the SECG signals collected from a 12-lead surface ECG system are used as an example in the following description to demonstrate the disclosed method 200. A person of skilled in the art will recognize that a similar methodology can be used with IECG signals collected from an IC system, or other EP signals collected from other areas of the body.

Figure 3:
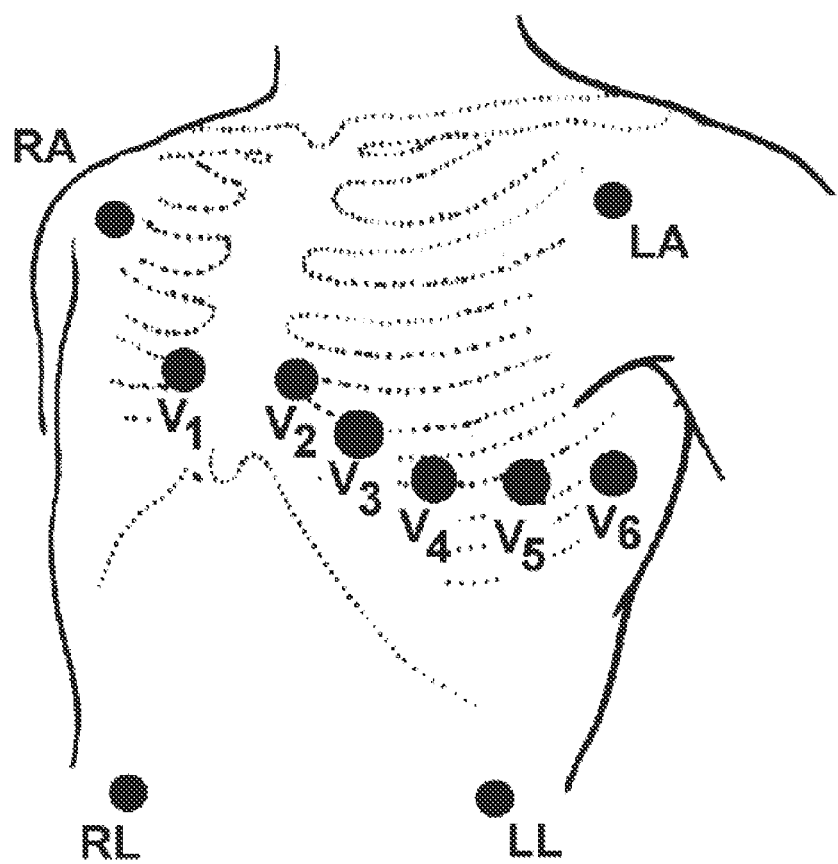
FIG. 3 illustrates a schematic diagram of example electrode positions of a standard 12-lead surface ECG system on a patient in accordance with some embodiments.

Referring to FIG. 3, a schematic diagram of example electrode positions of a standard 12-lead surface ECG system on a patient is shown in accordance with some embodiments.

As shown, the standard 12-lead surface ECG system can include ten electrodes: three electrodes are attached on the patient's left arm (LA), right arm (RA), and left leg (LL) to measure the limb leads (I, II, and III) and augmented limb leads (aVR, aVL, and aVF), six electrodes are placed at various locations of the patient's chest to calculate the chest leads (V1, V2, V3, V4, V5, V6), and one electrode acting as the ground reference (neutral electrode) is placed on the patient's right leg (RL).

Electrodes I, II, III, aVR, aVL, and aVF are six frontal plane leads, and electrodes V1, V2, V3, V4, V5, V6 are six chest leads. Three frontal plane leads are bipolar leads (I, II, and III), and three are augmented leads (aVR, aVL, and aVF). Of these six frontal plane leads, only two leads need to be known to calculate the remaining four.

In some embodiments, the collected ECG signals have a high sampling rate in a range between 400 Hz to 3000 Hz, such as 500 Hz, 800 Hz, 2000 Hz, etc. In some embodiments, the ECG signals can be collected over one or more continuous or intermittent sampling time periods. In some embodiments, the sampling time period can be determined based on the type and location of individual electrodes, and can have a sufficiently long timescale relative to the sampling rate of the individual electrode. For example, each sampling time period can be in a range from 5 seconds to 30 seconds.

Referring back to FIG. 2, method 200 can proceed to operation 220, in which relationships between EP signals of each pair of electrodes over one or more sampling time periods can be determined.

In some embodiments, the relationships between cardiac EP signals are biological signaling latencies between leads. In such embodiments, a cross-correlation between two ECG signals can be used to statistically describe a time delay or latency between ECG signals. For example, referring to FIG. 4, the cross-correlations between each pair of ECG signals collected from the 12 electrodes (I, II, III, aVR, aVL, aVF, V1, V2, V3, V4, V5, and V6) can form a square matrix. In this example, the ECG signal data used to generate the square matrix is acquired from the PhysioNet 2020 Challenge Training Dataset, with a 500 Hz sampling rate and a 10-second sampling time period. It is noted that the length of each ECG signal sampling period can be enlarged and the number of ECG signal sampling periods can be increased to gather more data over time.

Figure 4:
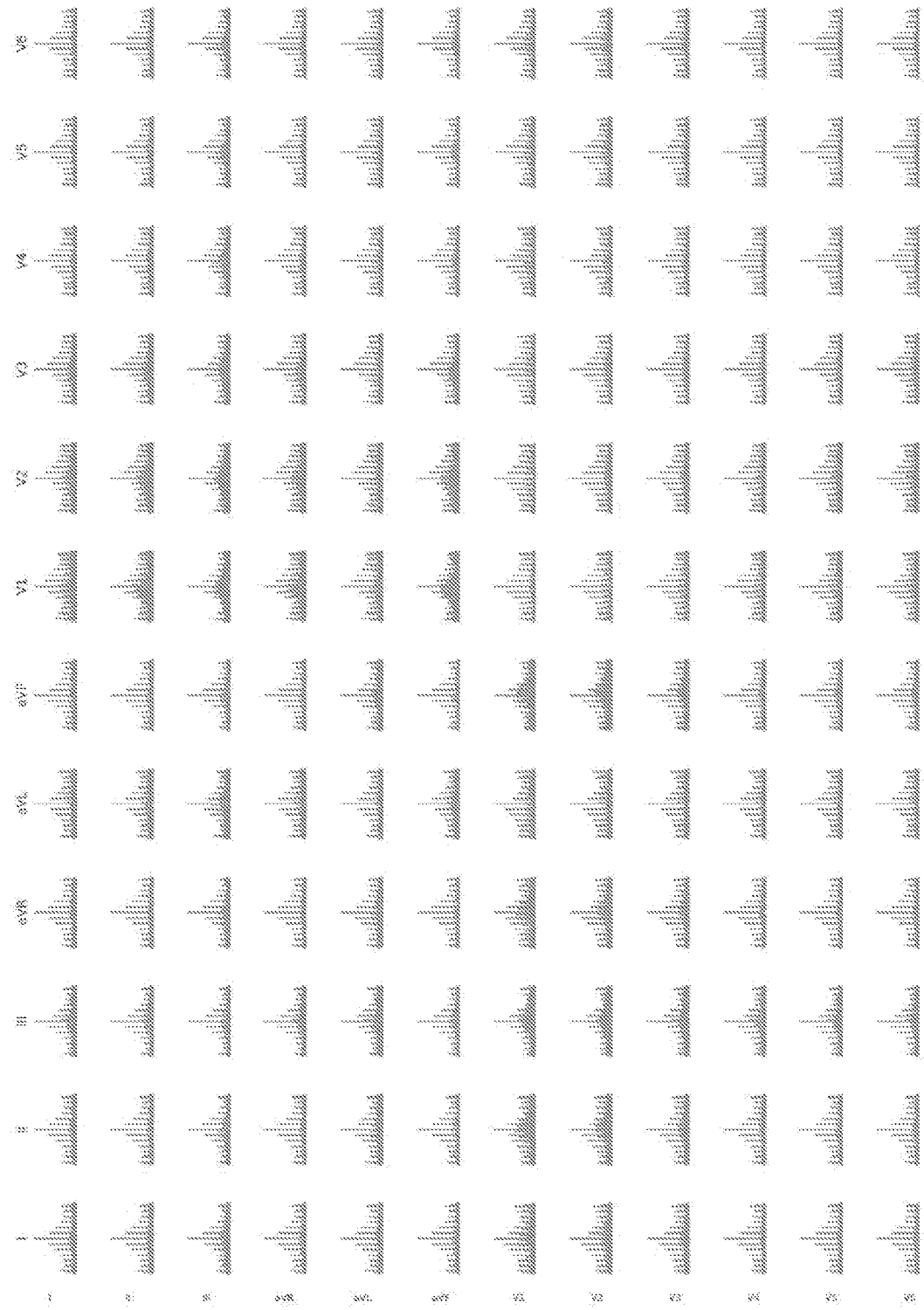
FIG. 4 illustrates an example square matrix of cross-correlations between each pair of SECG signals collected from a 12-lead surface ECG system, in accordance with some embodiments of the disclosed subject matter.

As shown in FIG. 4, each matrix element is a waveform signal cross-correlation, wherein the X-axis of each waveform represents time difference, while the Y-axis of each waveform represents a strength of the cross-correlation for that time difference between the two ECG signals. The waveform signal cross-correlation can be used to measure similarity between two ECG signals at different time scales. In some embodiments, standard statistical measurement of a shifting of the multiplicative amplitude each of the ECG signals relative to the other ECG signals, represented by the waveform signal cross-correlation, can be used to measure the time delay or latency between the pair of ECG signals over the sampling time period.

As one example shown in FIG. 4, the peak of cross-correlation in one matrix element coincides with the diagonal matrix element, which means ECG signals cross-correlate well with themselves. As another example, for a pair of ECG signals that are shifted by a relatively small time lag or latency relative to each other, the peak cross-correlative amplitude in the one matrix element between the pair of ECG signals can be close to the zero second (i.e., the 0 point of the X-axis). That is, if the peak cross-correlative amplitude of the one matrix element between the pair of ECG signals is not precisely at zero seconds, there is a small time delay between the pair of ECG signals.

In some alternative embodiments, the relationships between EP signals are Pearson correlation coefficients between leads. If the distance between two leads (e.g., IC leads) is relatively small, a Pearson correlation between two IECG signals, for example, can be determined based on the acquired IECG signals with a relatively high sampling rate over one or more sampling time periods to statistically measure a linear correlation between the two IECG signals. Since two IC leads can be relatively close together relative to the nerve signaling speed, the Pearson correlation coefficients between each pair of IECG signals can be used to measure the relative time delays or latencies between the corresponding pair of IC leads.

Accordingly, at operation 220 of FIG. 2, a matrix of relationships (e.g., biological signaling latencies and/or Pearson correlation coefficients as described above) between EP signals of each pair of electrodes can be constructed. In some embodiments, the matrix of relationships can be determined in real-time over moving windows of the one or more sampling time periods or the entire sampling time periods.

As shown in FIG. 2, method 200 can proceed to operation 230, in which a geometry of the multiple electrodes can be reconstructed based on the relationships between EP signals.

In some embodiments, when the relationships between EP signals are time lags between SECG leads, a physical distance between each pair of surface electrodes can be determined based on the time lag between the corresponding ECG signals of the pair of electrodes.

Physiologically, the signal latencies between two electrodes can be associated with a spatial distance of the two electrodes. For example, the signal latency multiplied by the known right atrial nerve conduction speeds (e.g., 13 m/s to 20 m/s) can be very close to the lead separations, e.g., within a small order. Under an implicit assumption that two physically separated electrodes connected to a common medium have an intrinsic signal latency proportional to the physical distance of the electrodes, a spatial map of the multiple electrodes can be generated based on the time lags between EP signals.

For example, a weighted graph of the multiple electrodes can be first generated based on the time lags between EP signals, by using the multiple electrodes as nodes in the weighted graph and using the time lags between each pair of electrodes as weighted edges between each pair of corresponding nodes. The weighted graph can then be run through any suitable fitting algorithm to determine the spatial relationships of the multiple electrodes.

In some embodiments, the fitting algorithm can be the Fruchterman-Reingold optimization method, which can position the nodes of the weighted graph in a two-dimensional (2D) or three-dimensional (3D) embedding space. In the fitted geometrically and/or spatially weighted graph, the distances between the nodes in the 2D or 3D embedded space are proportional to the weights on the edges between nodes. One of skilled in the art will recognize that other fitting algorithms can also be used without departing from the spirit and scope of the present embodiments.

Referring to FIGS. 5A-5J, ten schematic diagrams illustrate ten example 2D spatial maps of six chest leads V1, V2, V3, V4, V5, V6, in accordance with some embodiments of the disclosed subject matter. It is noted that the ten exemplary 2D spatial maps are generated based on SECG signal data of variety of patients, some with cardiac conditions and others without cardiac conditions. The SECG signal data used in these example maps are acquired from the PhysioNet 2020 Challenge Training Dataset, with a 500 Hz sampling rate and over 10-25 seconds sampling time periods. As shown in FIGS. 5A-5J, each of the six chest leads V1, V2, V3, V4, V5, V6 in the 2D spatial map is a node and the weighted edge between two nodes represents a time lag and a physical distance between the two corresponding surface electrodes. Additional details regarding each of these figures are provided further below.

In some alternative embodiments, when the relationships between EP signals are Pearson correlation coefficients between IC (or other closely-positioned) leads, dimensionless weights are generated on the edges of a weighted graph instead of the full temporal time latencies. Thus, a relative distance rather than an actual physical distance between the IC electrodes can be reconstructed based on the Pearson correlation coefficients. As discussed above, a physical distance between two IC leads can be relatively small, thus Pearson correlation is a useful technique to reconstruct the relative spatial relationship between IC leads.

Figure 6B:
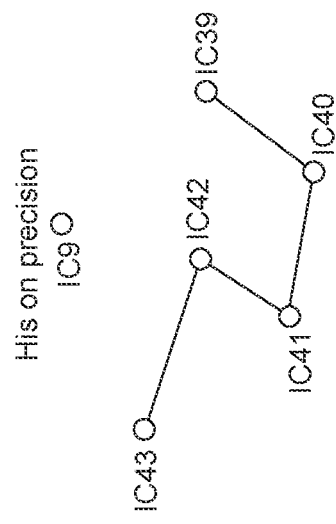
FIGS. 6A-6V illustrate reconstructed 2D spatial maps of five example intracardiac leads, in accordance with some embodiments of the disclosed subject matter.
Figure 6D:
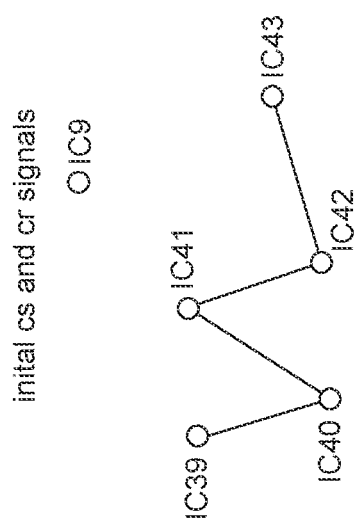
Figure 6A:
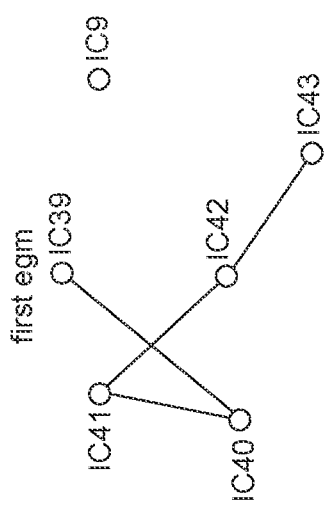
Figure 6C:
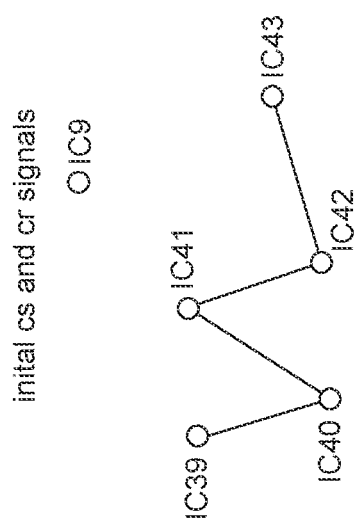
Figure 6F:
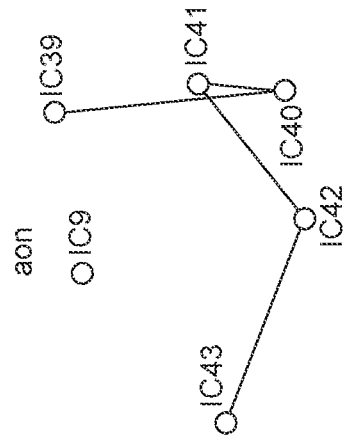
Figure 6H:
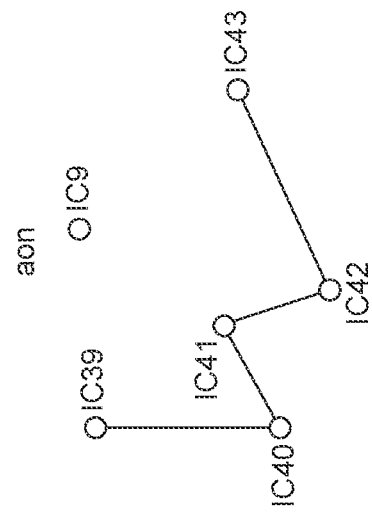
Figure 6E:
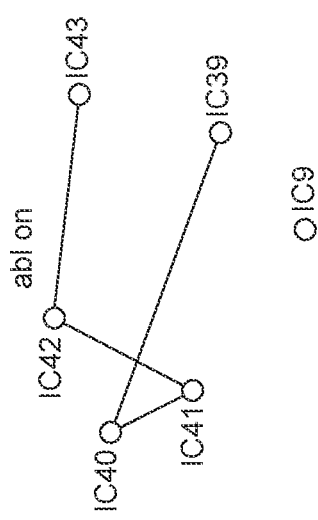
Figure 6G:
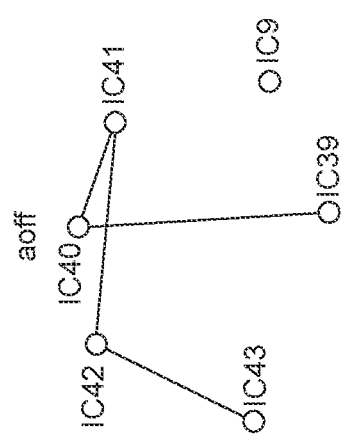
Figure 6N:
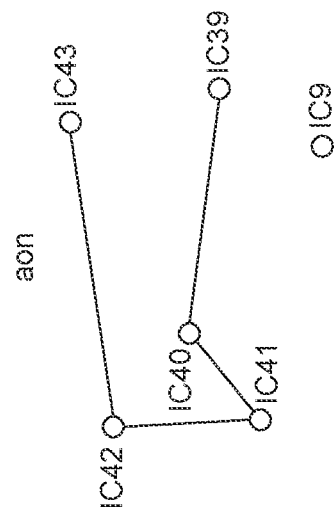
Figure 6P:
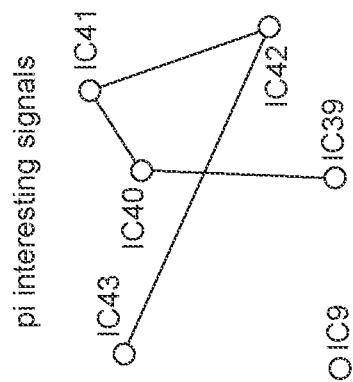
Figure 6M:
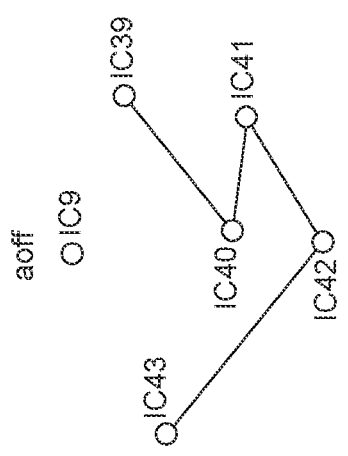
Figure 6O:
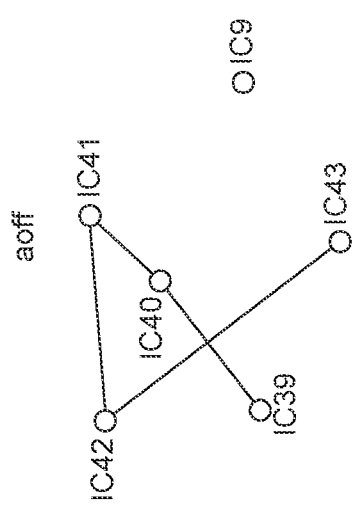
Figure 6R:
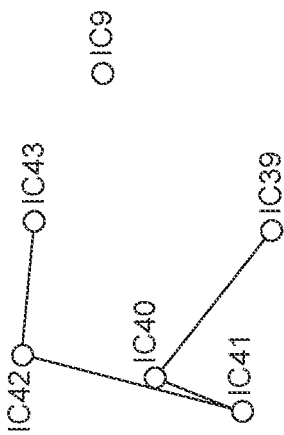
Figure 6T:
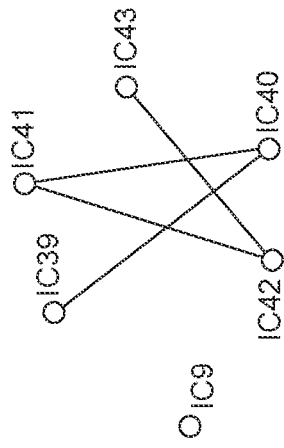
Figure 6Q:
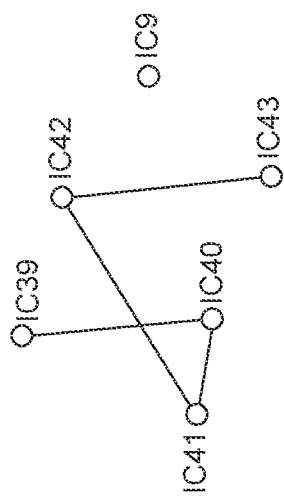
Figure 6S:
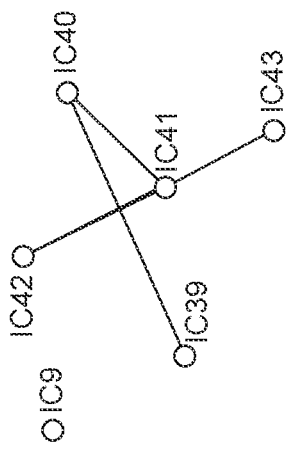
Figure 7A:
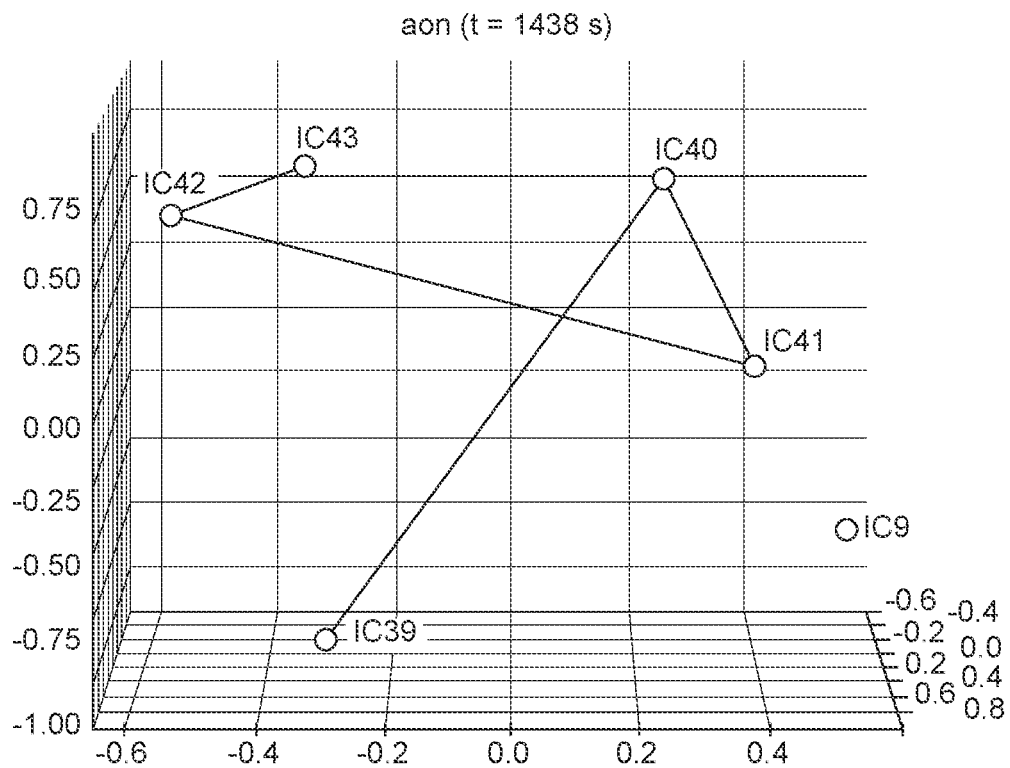
FIGS. 7A-7J illustrate reconstructed 3D spatial maps of five example intracardiac leads, in accordance with some embodiments of the disclosed subject matter.
Figure 7B:
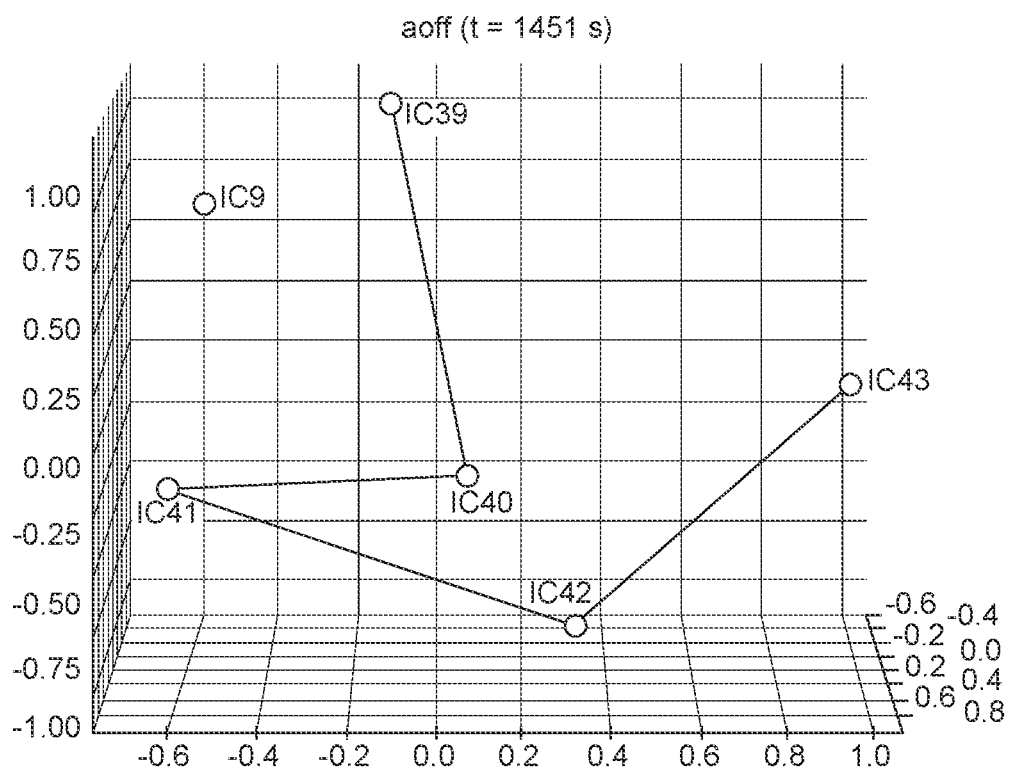
Figure 7C:
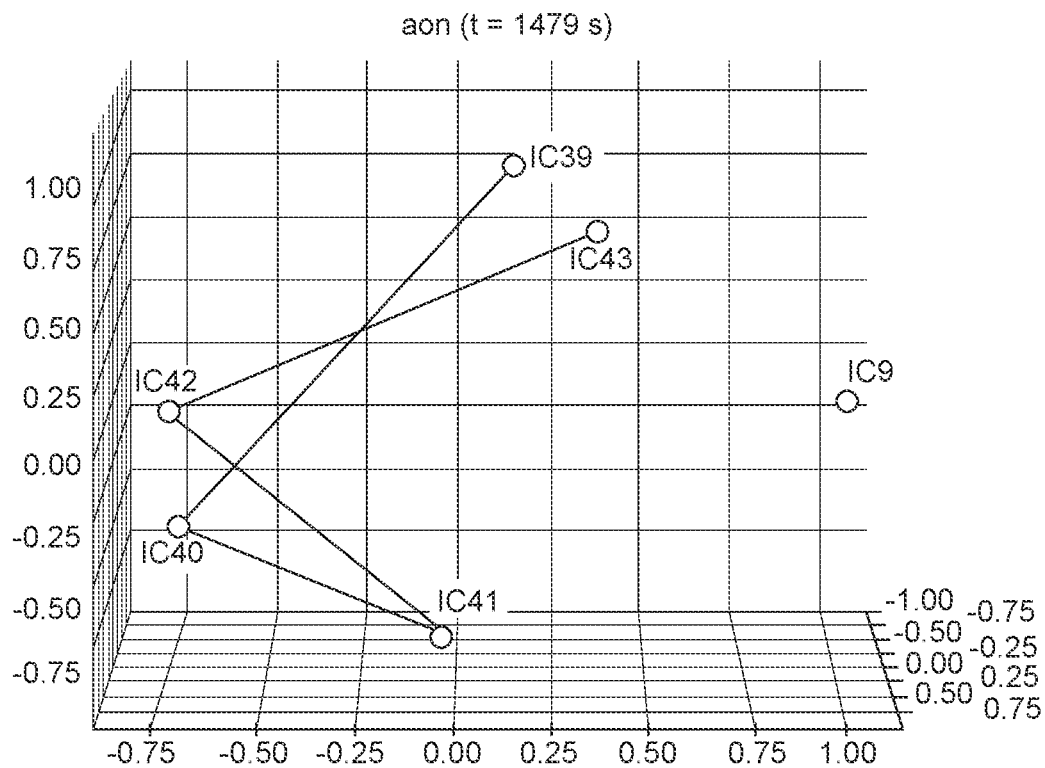
Figure 7D:
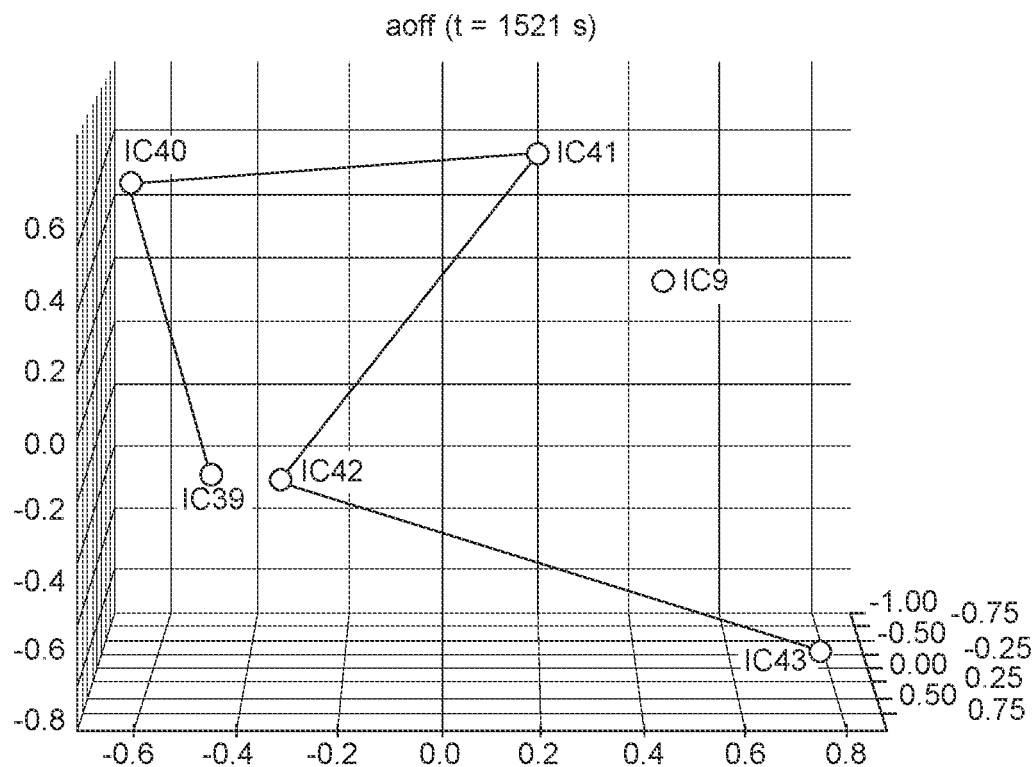
Figure 7E:
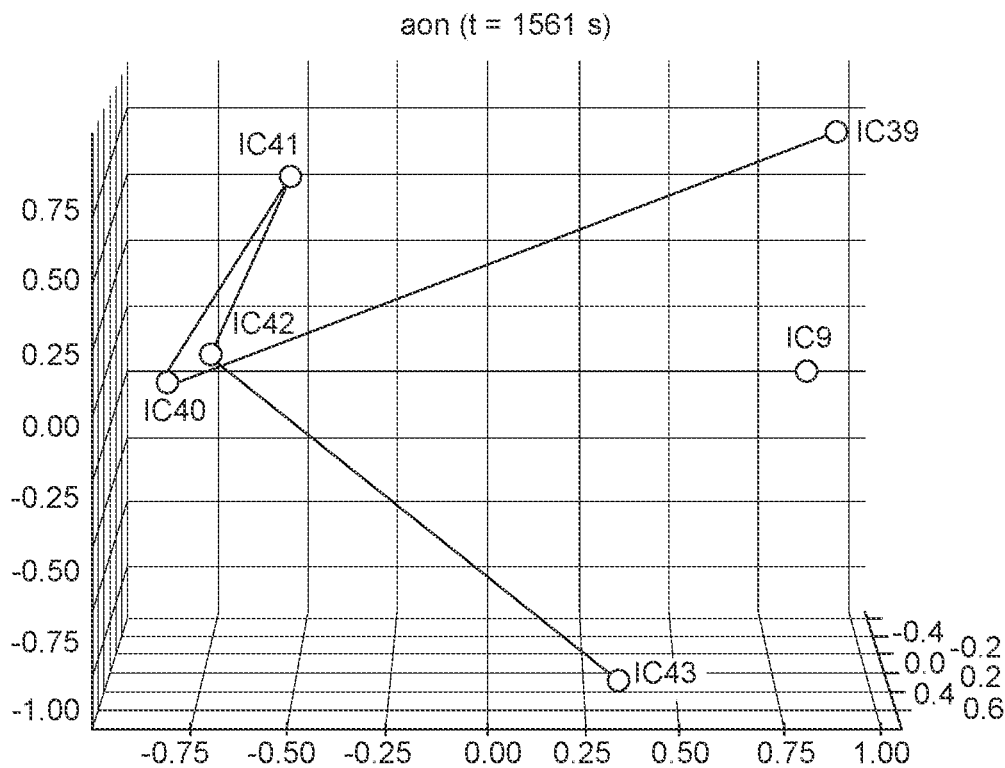
Figure 7F:
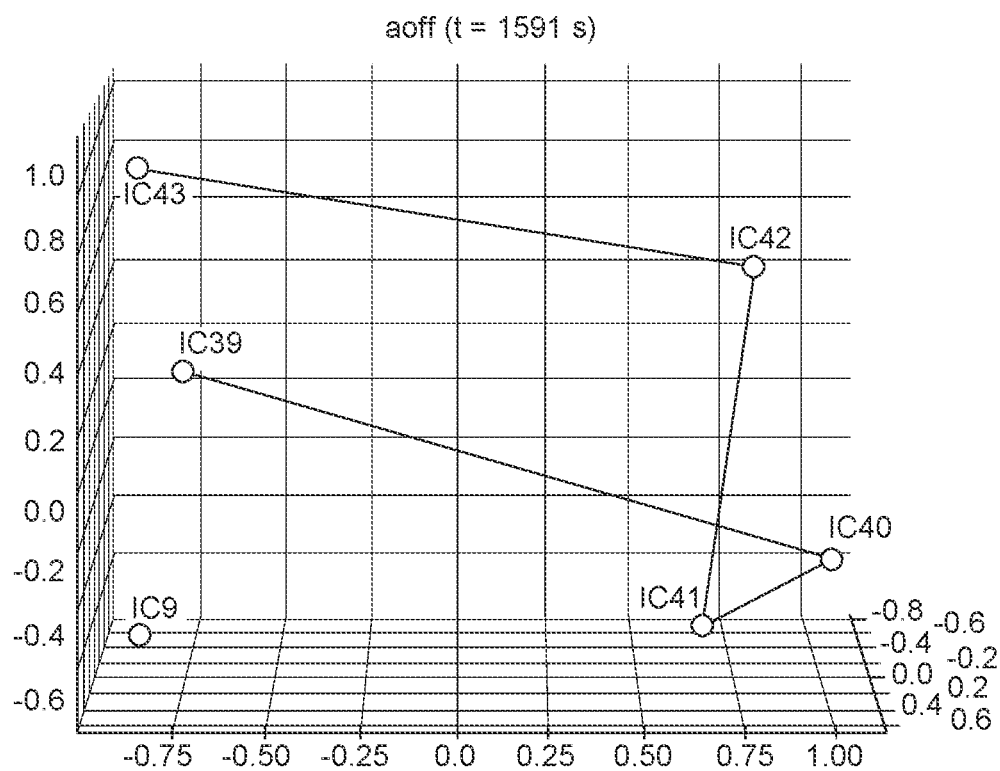
Figure 7G:
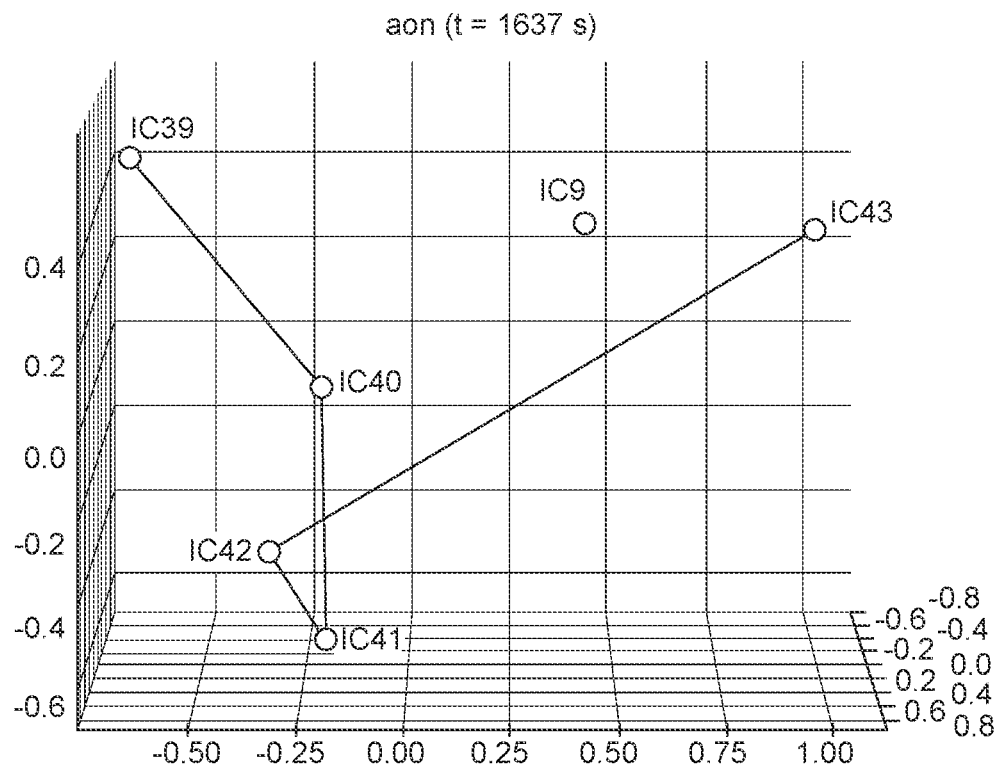
Figure 7H:
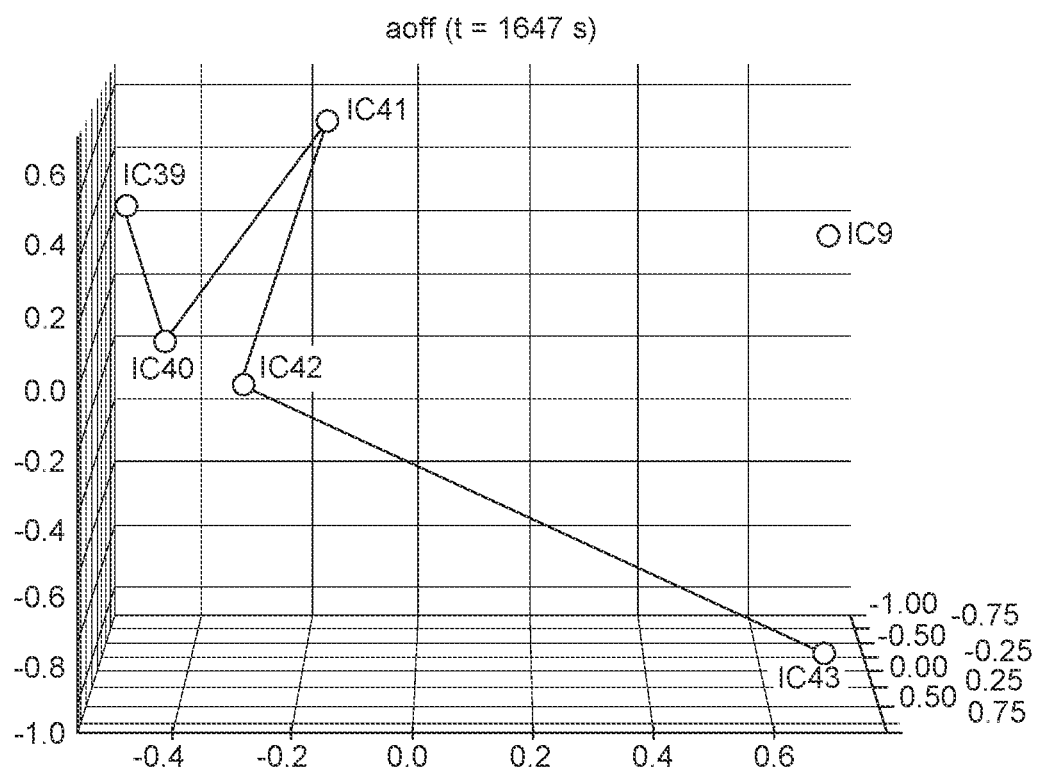
Figure 7I:
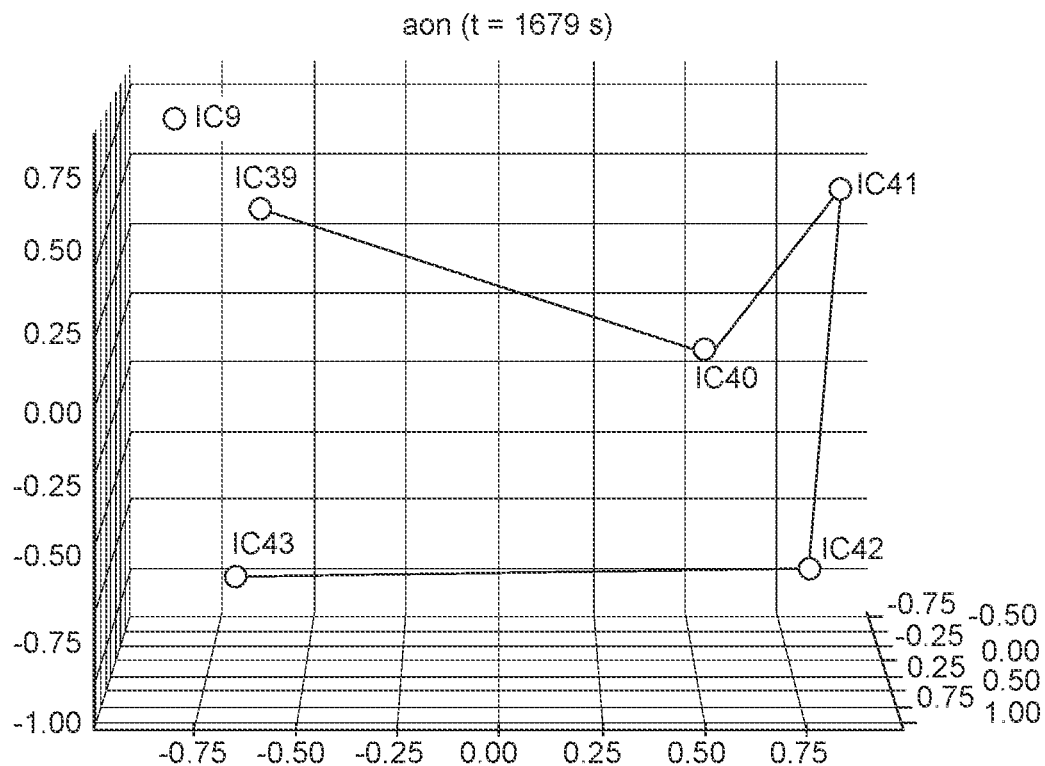
Figure 7J:
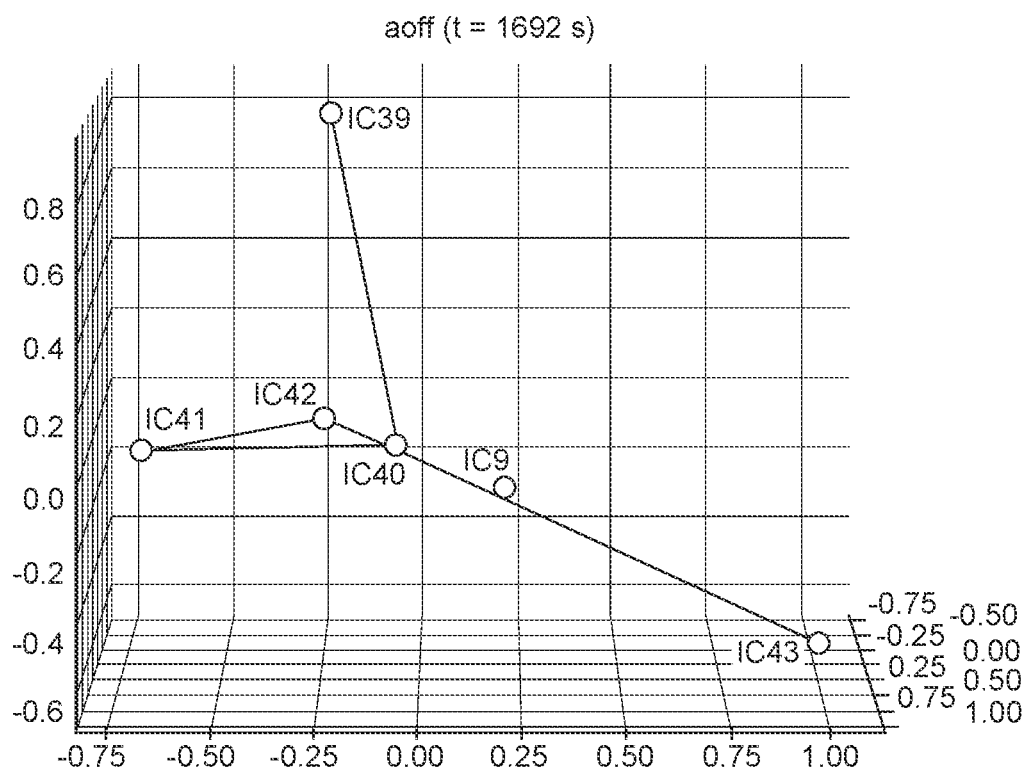

Referring to FIGS. 6A-6V, 22 schematic diagrams illustrate 22 exemplary 2D spatial maps of five intracardiac leads IC9, IC43, IC42, IC41, IC40 and IC39, in accordance with some embodiments of the disclosed subject matter. Referring to FIGS. 7A-7J, 10 schematic diagrams illustrate 10 exemplary 3D spatial maps of five intracardiac leads IC9, IC43, IC42, IC41, IC40 and IC39, in accordance with some embodiments of the disclosed subject matter. The 2D spatial maps as shown in FIGS. 6A-6V and the 3D spatial maps as shown in FIGS. 7A-7J are generated based on IECG signal data of a patient over multiple 500-second windows around annotated events. The fitting algorithm for these examples is a Fruchterman-Reingold optimization method with 50K iterations based on Pearson correlations between each pair of the five intracardiac leads. As shown in FIGS. 6A-6V and 7A-7J, each of the five intracardiac leads IC9, IC43, IC42, IC41, IC40 and IC39 in the 2D and 3D spatial maps is a node and the weighted edge between two nodes represents a relative time lag and a relative distance between the two corresponding intracardiac leads.

Referring back to FIG. 2, method 200 can proceed to operation 240, in which classification of patient condition can be determined based on the reconstructed geometry of the multiple electrodes.

Figure 5A:
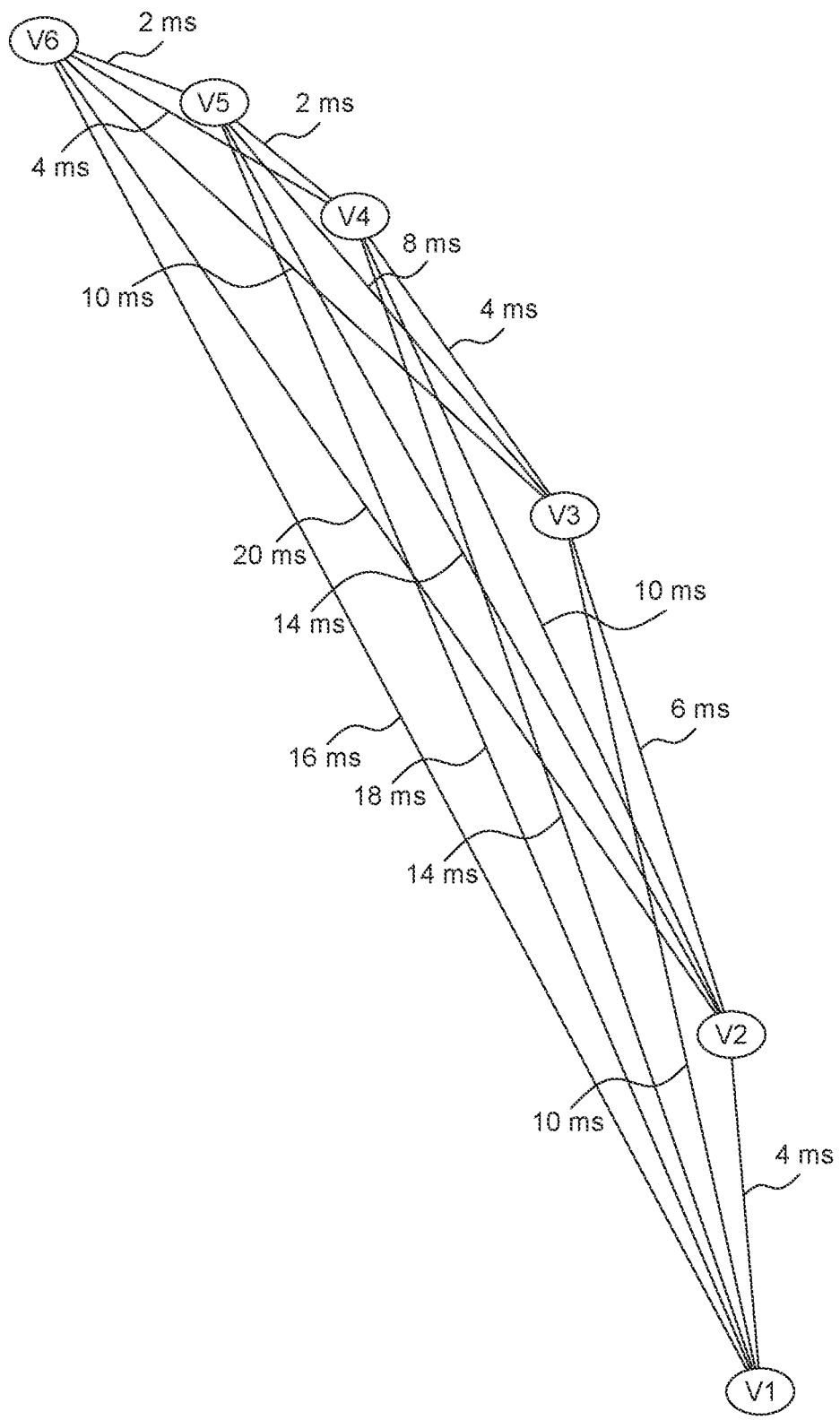
FIGS. 5A-5J illustrate reconstructed 2D spatial maps of six example chest leads, in accordance with some embodiments of the disclosed subject matter.
Figure 5B:
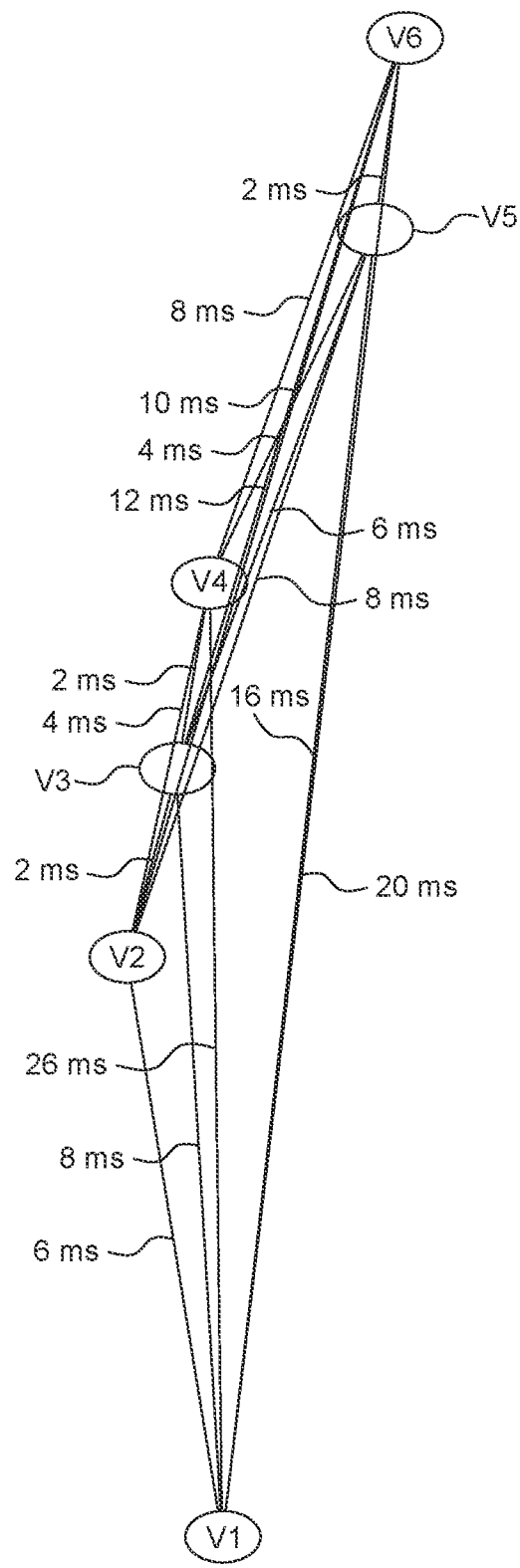
Figure 5C:
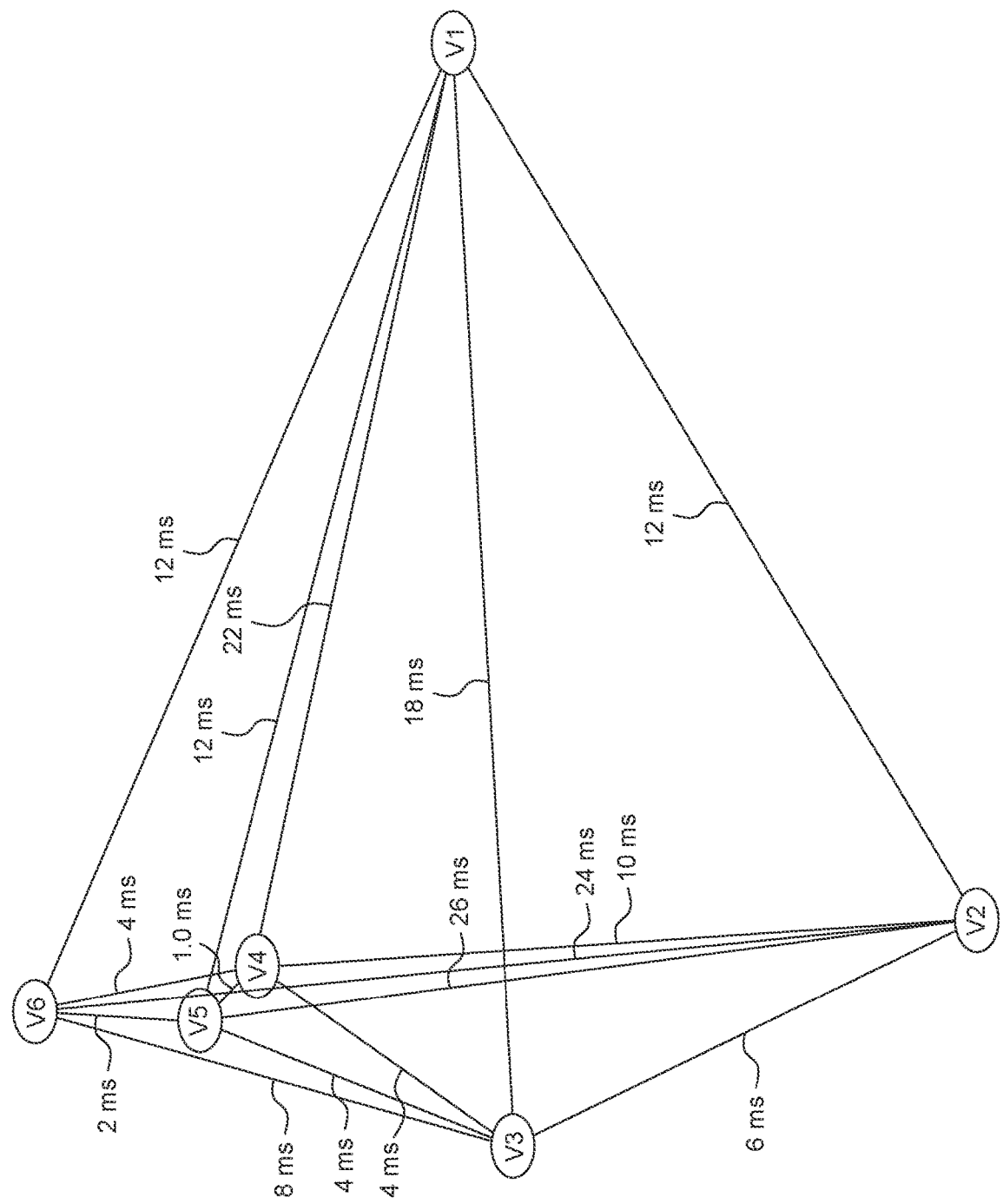
Figure 5D:
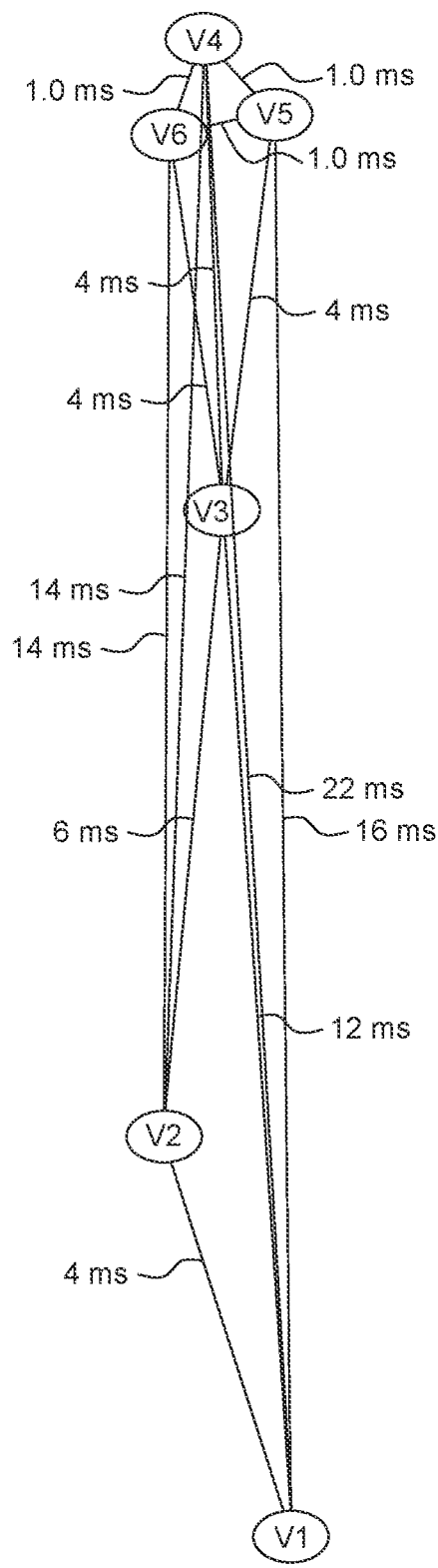
Figure 5E:
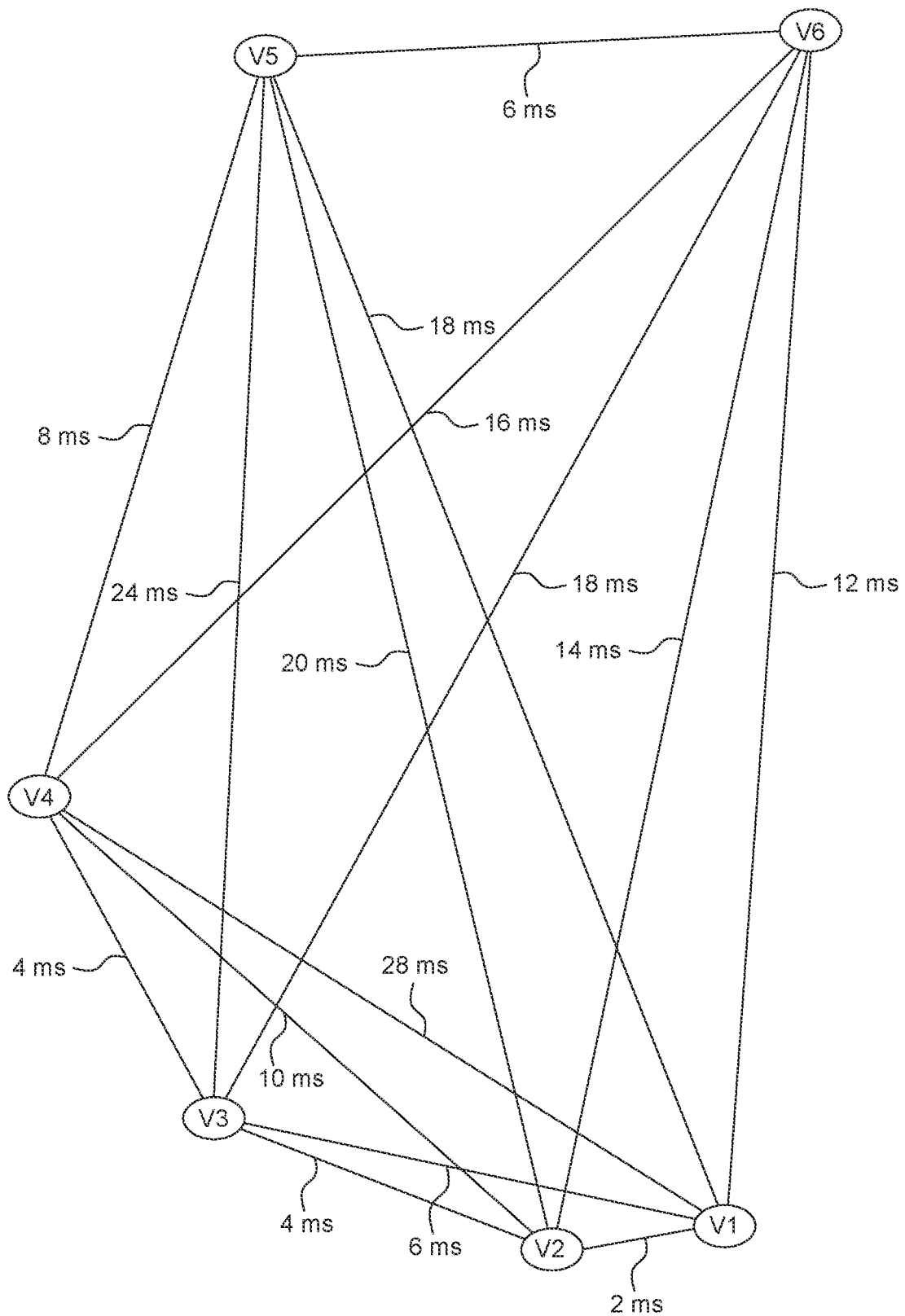
Figure 5F:
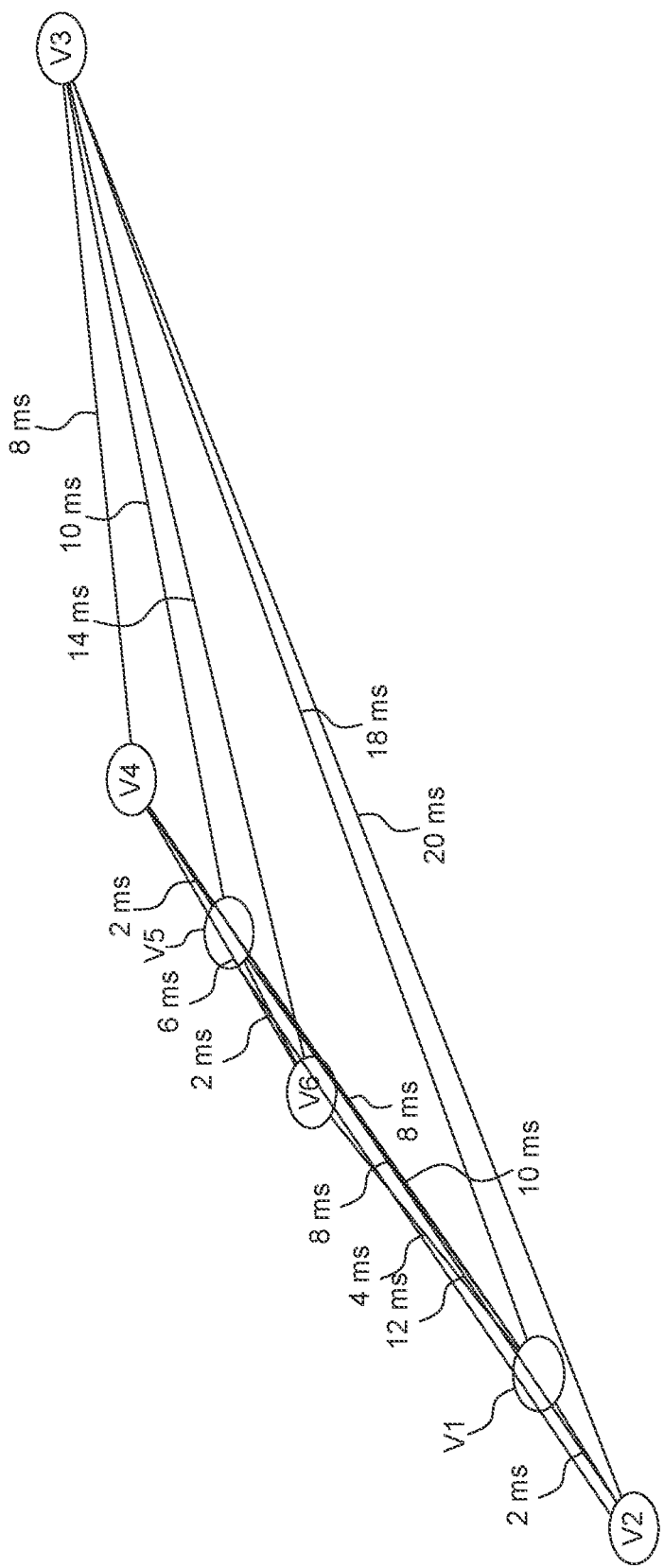
Figure 5G:
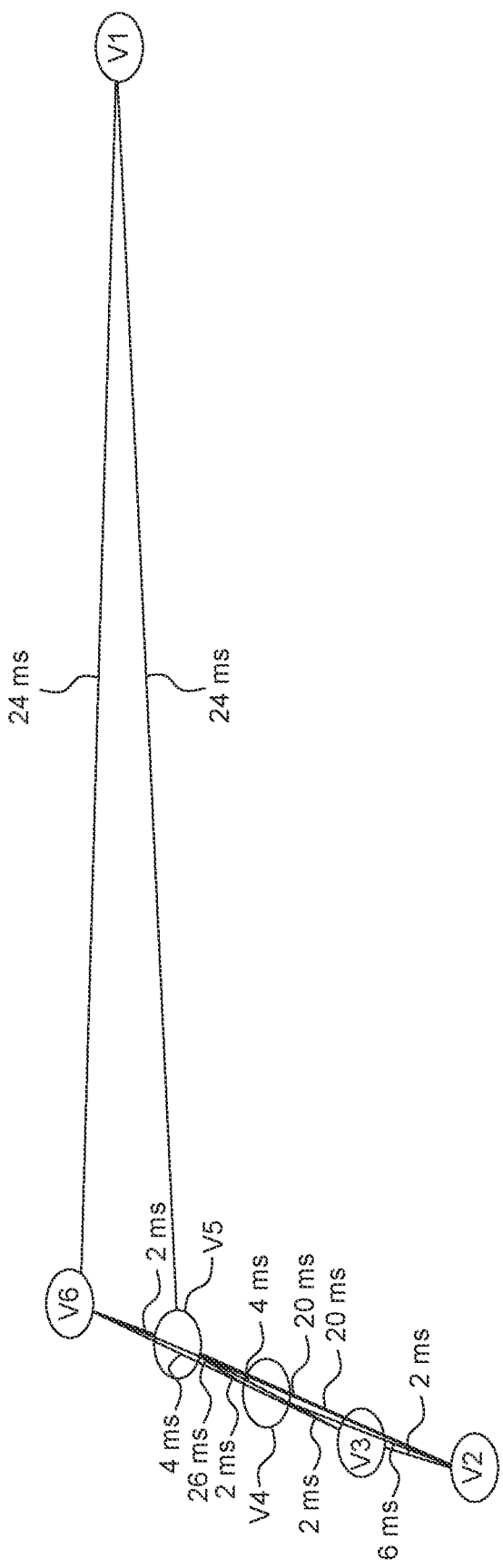
Figure 5H:
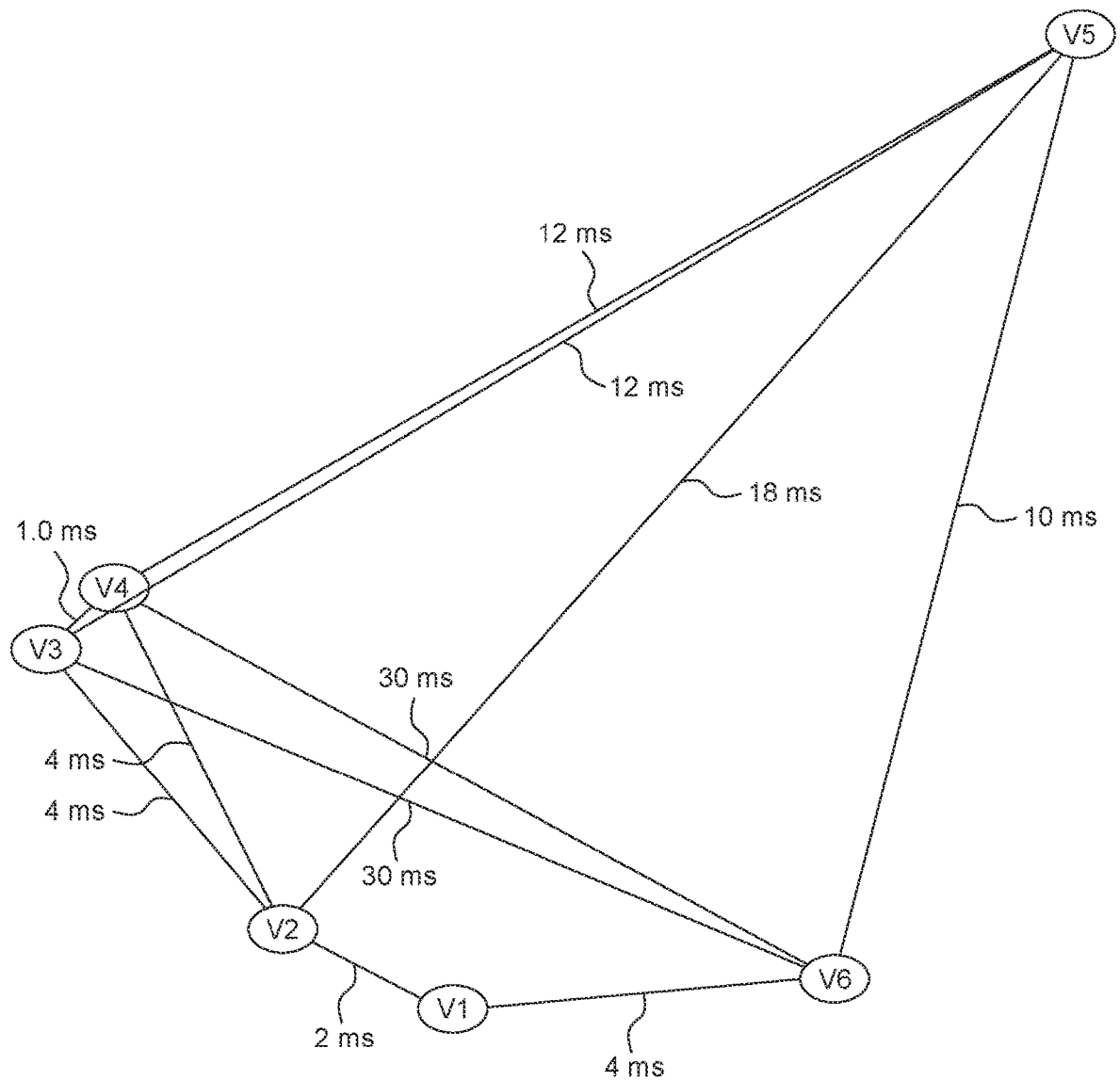
Figure 5I:
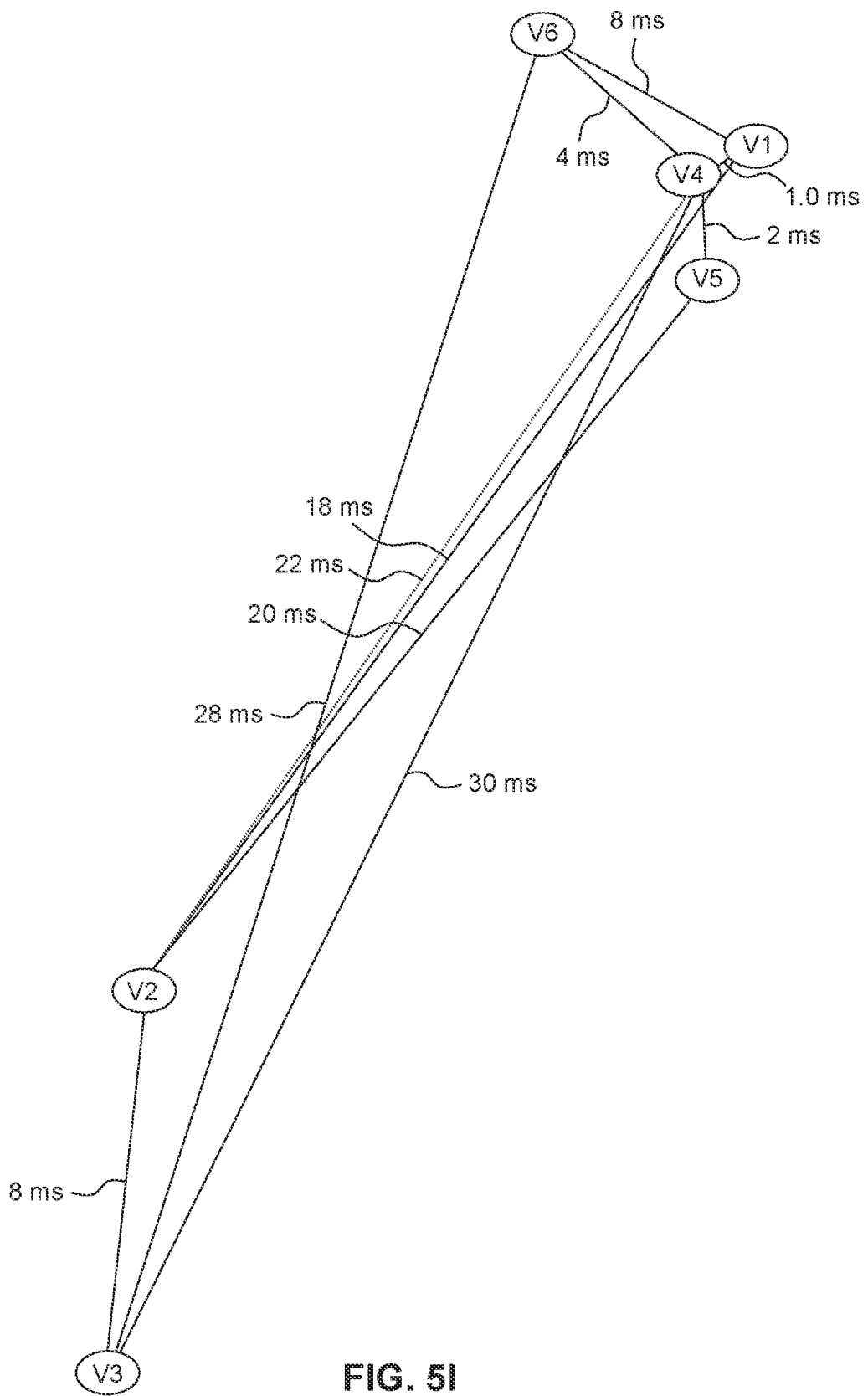
Figure 5J:
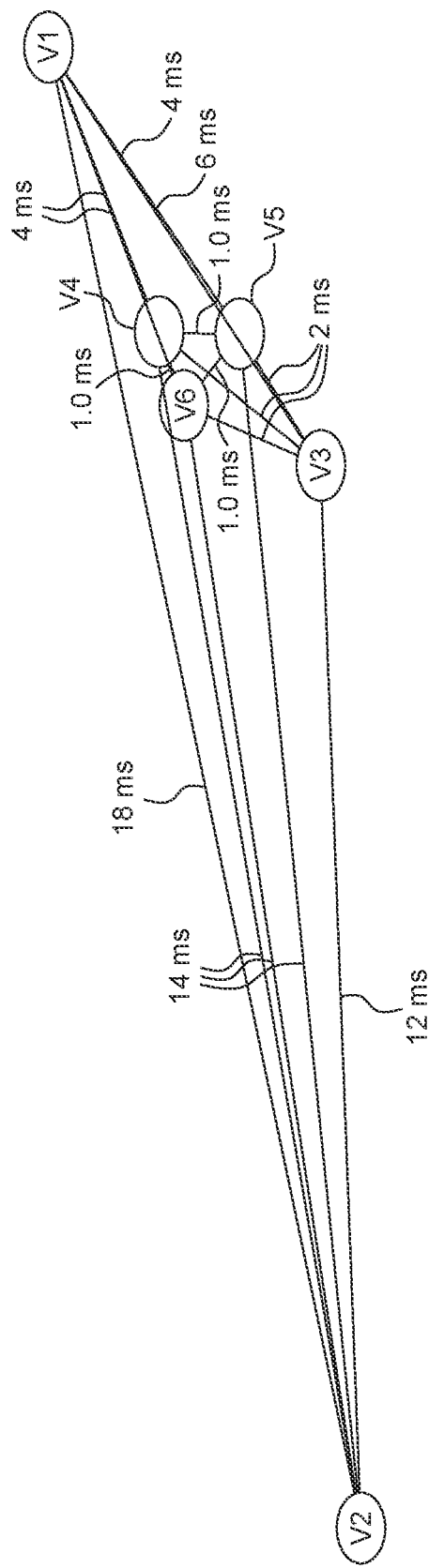

In some embodiments, a normal condition and various abnormalities can be indicated by various geometries of the reconstructed spatial map of multiple EP electrodes. For example, in some embodiments, a normal cardiac condition and various cardiac abnormalities can be indicated by various geometries of the reconstructed spatial map of multiple ECG electrodes. For example, as shown in FIG. 5A, the reconstructed positions of the six chest leads V1-V6 in the reconstructed 2D spatial map forms a curve around the patient's recordable chest area, which indicate that the patient corresponding to FIG. 5A has a normal cardiac condition. In contrast, as shown in FIGS. 5B, 5C and 5H, the six chest leads V1-V6 in each reconstructed 2D spatial map are positioned in a correct order but either form an approximate straight line rather than a curve, or form a curve with visible distortions. Such distortions indicate that each of the three patients corresponding to FIGS. 5B, 5C and 5H may have an atrial fibrillation condition. As shown in FIG. 5D, the six chest leads V1-V6 in the reconstructed 2D spatial map are not positioned in a correct order, which may indicate that the patient has a premature ventricular contraction (PVC) condition. As shown in FIGS. 5F, 5G and 5I, the six chest leads V1-V6 in the reconstructed 2D spatial maps are not positioned in a correct order, and lead V1 or V3 has a significantly larger time lag as compared with the other five leads. Such a feature indicates that each of the three patients corresponding to FIGS. 5F, 5G and 5I may have a right bundle branch block (BBB) condition. As shown in FIG. 5J, the six chest leads V1-V6 in the reconstructed 2D spatial map are not positioned in a correct order, and lead V2 has a significantly larger time lag with respect to the other five leads. Such a feature indicates that the patient corresponding to FIG. 5J may have an ST-segment depression condition.

It is noted that FIGS. 5A-5J and the features of the reconstructed 2D spatial maps of the six chest leads V1-V6 discussed above are only used as examples for demonstrative purposes, but do not limit the relationships between various geometries of the multiple electrodes and various cardiac conditions. In some other embodiments, any other common features in the reconstructed 2D or 3D spatial maps of the electrodes that are associated with certain cardiac conditions can be used to identify classifications of patient cardiac conditions. In some embodiments, machine learning techniques can be applied to enhance the ability to diagnose cardiac conditions based on the reconstructed geometry of the multiple electrodes.

It is also noted that, when the EP signals are other types of EP signals, such as electroneuronographic (ENOG) signals, electroencephalographic (EEG) signals, electromyographic (EMG) signals, electrooculography (EOG) signals, electrocochleographic (ECOG) signals, electrogastrographic (EGG) signals, electrogastroenterographic (EGEG) signals, electrohysterographic (EHG) signals, electropneumographic (EPG) signals, electrospinographic (ESG) signals, etc., classifications of patient conditions of specific region(s), tissue(s), and/or organ(s) of the patient can be determined based on the reconstructed geometry of multiple corresponding electrodes of the various types of EP signals, respectively. Proper mappings between various reconstructed geometries of different types of electrodes and various classifications of patient conditions of specific region(s), tissue(s), and/or organ(s) of the patient can be determined by a person skilled in the art, or can be determined by any suitable machine learn techniques.

Referring back to FIG. 2, after reconstructing the geometry of the multiple electrodes at operation 230, method 200 can alternatively proceed to operation 250, in which misplacement of one or more electrodes can be determined based on the reconstructed geometry of the multiple electrodes.

It is noted that a Fruchterman-Reingold optimization in 3D embedding space can be used to register the multiple fits to common known positions, scales and orientations. Since the spatial reconstruction is sensitive to the misplaced lead positions, any lead placement errors, such as accidentally swapping two of the lead positions, misaligned vector orientations between lead patches, sub-optimal lead placement, etc., can be identified based on the reconstructed 3D spatial map of the electrodes.

Further, the positions of the multiple electrodes may not be guaranteed to be stationary over time. For example, the intracardiac leads may move over the course of a surgery. In such a scenario, a real-time 3D spatial map of the IC leads can be reconstructed during moving windows, so that a potential movement of one or more intracardiac leads can be monitored, and the optimal lead placement can be automatically recommended.

It is noted that method 200 can be performed by processing logic that can comprise hardware (e.g., circuitry, dedicated logic, programmable logic, microcode, etc.), software (e.g., instructions executing on a processing device), or a combination thereof. It is to be appreciated that not all operations may be needed to perform the disclosure provided herein. Further, some of the steps may be performed simultaneously, or in a different order than shown in FIG. 2, as will be understood by a person of ordinary skill in the art.

Based on the teachings contained in this disclosure, it will be apparent to persons skilled in the relevant art how to make and use embodiments of this disclosure using data processing devices, computer systems, or computer architectures other than that shown in FIG. 50. In particular, embodiments can operate with software, hardware, and/or operating system implementations other than those described herein.

Accordingly, methods, systems, and media for reconstructing bioelectronic lead placement are provided. By analyzing the time lag correlations between raw bioelectronic signals from multiple electrodes, (e.g., the surface cardiac electrodes, intracardiac electrodes, and/or any other suitable EP electrodes) without knowing any other information, a spatial distribution of the multiple electrodes can be reconstructed based on a fitted weighted graph in which the electrodes are nodes and the time lag relationships are edges. Based on the reconstructed spatial distribution of multiple electrodes, faulty or sub-optimal lead placement can be automatically identified, optimal lead placement can be automatically recommended, a summary of EP signal recordings can be provided, and automated classification of patient conditions can be visually simplified.

It is to be appreciated that the Detailed Description section, and not any other section, is intended to be used to interpret the claims. Other sections can set forth one or more but not all exemplary embodiments as contemplated by the inventor(s), and thus, are not intended to limit this disclosure or the appended claims in any way.

While this disclosure describes exemplary embodiments for exemplary fields and applications, it should be understood that the disclosure is not limited thereto. Other embodiments and modifications thereto are possible, and are within the scope and spirit of this disclosure. For example, and without limiting the generality of this paragraph, embodiments are not limited to the software, hardware, firmware, or entities illustrated in the figures and or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments can perform functional blocks, steps, operations, methods, etc. using orderings different than those described herein. This disclosure also extends to methods associated with using or otherwise implementing the features of the disclosed hardware and systems herein.

The breadth and scope of this disclosure should not be limited by any of the above-described exemplary embodiments, but should be defined only in accordance with the following claims and their equivalents.

What is claimed is:

1. A system for reconstructing bioelectronic lead placement, comprising:
 a processor configured to:
  receive electrophysiology (EP) signals from a plurality of electrodes, the plurality of electrodes having been positioned on a patient's body for collection of the EP signals;
  determine biological signaling time latencies between the EP signals from one or more pairs of the plurality of electrodes over one or more sampling time periods;
  generate a weighted graph of the plurality of electrodes based on the biological signaling time latencies;
  determine, based on the weighted graph and known positions, scales, or orientations of electrodes, that one or more of the plurality of electrodes on the patient are misplaced so as to yield an incorrect reading; and
  correct a misplacement of the plurality of electrodes based on the determination that the one or more of the plurality of electrodes on the patient are misplaced.

2. The system of claim 1, wherein the plurality of electrodes includes surface electrodes configured to collect surface electrocardiogram (SECG) signals.

3. The system of claim 1, wherein the plurality of electrodes includes intracardiac electrodes configured to collect intracardiac electrocardiogram (IECG) signals.

4. The system of claim 1, wherein to generate the weighted graph, the processor is further configured to fit the biological signaling time latencies to the weighted graph using a fitting function, wherein the plurality of electrodes are nodes in the weighted graph and the biological signaling time latencies are edges in the weighted graph.

5. The system of claim 4, wherein the fitting function is a Fruchterman-Reingold optimization method, and the processor is further configured to fit the biological signaling time latencies to the weighted graph in a two or three dimensional embedded space using the fitting function.

6. The system of claim 1, wherein the processor is further configured to determine a classification of a patient condition based on the correction of the misplacement of the plurality of electrodes.

7. The system of claim 1, wherein to correct the misplacement of the plurality of electrodes, the processor is further configured to correct a misplacement of at least one of two electrodes of the plurality of electrodes to fix a vector orientation between the two electrodes.

8. The system of claim 7, wherein to correct the misplacement of the plurality of electrodes, the processor is further configured to indicate a change in placement of one or more electrodes in the plurality of electrodes.

9. The system of claim 1, wherein the processor is further configured to determine the sampling time period based on a type and a location of each electrode in the plurality of electrodes.

10. The system of claim 1, wherein to determine the biological signaling time latencies between the EP signals from the one or more pairs of the plurality of electrodes, the processor is further configured to determine the biological signaling time latencies between the EP signals based on cross-correlations between each pair of EP signals.

11. A method for reconstructing bioelectronic lead placement, comprising:
acquiring electrophysiology (EP) signals collected from a plurality of electrodes, the plurality of electrodes having been positioned on a patient's body for collection of the EP signals;
determining biological signaling time latencies between the EP signals from one or more pairs of the plurality of electrodes over one or more sampling time periods;
generating a weighted graph of the plurality of electrodes based on the biological signaling time latencies;
determining, based on the weighted graph and known positions, scales, or orientations of electrodes, that one or more of the plurality of electrodes on the patient are misplaced so as to yield an incorrect reading; and
correct a misplacement of the plurality of electrodes based on the determining that the one or more of the plurality of electrodes on the patient are misplaced.

12. The method of claim 11, wherein:
the acquiring of the EP signals comprises acquiring surface electrocardiogram (SECG) signals; and
the plurality of electrodes includes surface electrodes.

13. The method of claim 11, wherein:
the acquiring of the EP signals comprises acquiring intracardiac electrocardiogram (IECG) signals; and
the plurality of electrodes includes intracardiac electrodes.

14. The method of claim 11, wherein the generating the weighted graph comprises:
fitting the biological signaling time latencies to the weighted graph using a fitting function, wherein the plurality of electrodes are nodes in the weighted graph and the biological signaling time latencies are edges in the weighted graph.

15. The method of claim 14, wherein the fitting function is a Fruchterman-Reingold optimization method, and further comprises:
fitting the biological signaling time latencies to the weighted graph in a two or three dimensional embedded space using the fitting function.

16. The method of claim 11, further comprising:
determining a classification of a patient condition based on the correcting of the misplacement of the plurality of electrodes.

17. The method of claim 11, wherein the correcting the misplacement of the plurality of electrodes comprises:
correcting a misplacement of at least one of two electrodes in the plurality of electrodes to fix a vector orientation between the two electrodes.

18. The method of claim 11, wherein the correcting the misplacement of the plurality of electrodes comprises:
indicating a change in placement of one or more electrodes in the plurality of electrodes.

19. The method of claim 11, further comprising:
determining the sampling time period based on a type and a location of each electrode in the plurality of electrodes.

20. The method of claim 11, wherein the determining the biological signaling time latencies between the EP signals from the one or more pairs of the plurality of electrodes comprises:
determining the biological signaling time latencies between the EP signals based on cross-correlations between each pair of EP signals.

21. A non-transitory computer-readable medium containing computer-executable instructions that, when executed by a hardware processor, cause the hardware processor to perform a method for reconstructing bioelectronic lead placement, the method comprising:
acquiring electrophysiology (EP) signals collected from a plurality of electrodes, the plurality of electrodes having been positioned on a patient's body for collection of the EP signals;
determining biological signaling time latencies between the EP signals from one or more pairs of the plurality of electrodes over one or more sampling time periods;
generating a weighted graph of the plurality of electrodes based on the biological signaling time latencies;
determining, based on the weighted graph and known positions, scales, or orientations of electrodes, that one or more of the plurality of electrodes on the patient are misplaced so as to yield an incorrect reading; and
correct a misplacement of the plurality of electrodes based on the determining that the one or more of the plurality of electrodes on the patient are misplaced.

22. The non-transitory computer-readable medium of claim 14, wherein:
the acquiring of the EP signals comprises acquiring surface electrocardiogram (SECG) signals; and
the plurality of electrodes includes surface electrodes.

23. The non-transitory computer-readable medium of claim 14, wherein:
the acquiring of the EP signals comprises acquiring intracardiac electrocardiogram (IECG) signals; and
the plurality of electrodes includes intracardiac electrodes.

24. The non-transitory computer-readable medium of claim 21, wherein the generating the weighted graph comprises:
fitting the biological signaling time latencies to the weighted graph using a fitting function, wherein the plurality of electrodes are nodes in the weighted graph and the biological signaling time latencies are edges in the weighted graph.

25. The non-transitory computer-readable medium of claim 24, wherein the fitting function is a Fruchterman-Reingold optimization method, and further comprises:
fitting the biological signaling time latencies to the weighted graph in a two or three dimensional embedded space using the fitting function.

26. The non-transitory computer-readable medium of claim 21, wherein the method further comprises:
determining a classification of a patient condition based on the correcting of the misplacement of the plurality of electrodes.

27. The non-transitory computer-readable medium of claim 21, wherein the correcting the misplacement of the plurality of electrodes comprises:

correcting a misplacement of at least one of two electrodes in the plurality of electrodes to fix a vector orientation between the two electrodes.

28. The non-transitory computer-readable medium of claim 21, wherein the correcting the misplacement of the plurality of electrodes comprises:
   indicating a change in placement of one or more electrodes in the plurality of electrodes.

29. The non-transitory computer-readable medium of claim 21, wherein the method further comprises:
   determining the sampling time period based on a type and a location of each electrode in the plurality of electrodes.

30. The non-transitory computer-readable medium of claim 21, wherein the determining the biological signaling time latencies between the EP signals from the one or more pairs of the plurality of electrodes comprises:
   determining the biological signaling time latencies between the EP signals based on cross-correlations between each pair of EP signals.

* * * * *